US009898659B2

(12) United States Patent
Kanagasingam et al.

(10) Patent No.: US 9,898,659 B2
(45) Date of Patent: Feb. 20, 2018

(54) SYSTEM AND METHOD FOR REMOTE MEDICAL DIAGNOSIS

(71) Applicant: COMMONWEALTH SCIENTIFIC AND INDUSTRIAL RESEARCH ORGANISATION, Campbell, Australian Capital Territory (AU)

(72) Inventors: Yogesan Kanagasingam, Floreat (AU); Di Xiao, Floreat (AU); Janardhan Vignarajan, Floreat (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 77 days.

(21) Appl. No.: 14/892,415

(22) PCT Filed: May 19, 2014

(86) PCT No.: PCT/AU2014/050043
§ 371 (c)(1),
(2) Date: Nov. 19, 2015

(87) PCT Pub. No.: WO2014/186838
PCT Pub. Date: Nov. 27, 2014

(65) Prior Publication Data
US 2016/0092721 A1 Mar. 31, 2016

(30) Foreign Application Priority Data
May 19, 2013 (AU) ................................ 2013901768

(51) Int. Cl.
*G06K 9/00* (2006.01)
*G06K 9/62* (2006.01)
(Continued)

(52) U.S. Cl.
CPC ......... *G06K 9/0061* (2013.01); *G06F 19/328* (2013.01); *G06F 19/345* (2013.01);
(Continued)

(58) Field of Classification Search
CPC ......... G06T 7/0012; G06T 7/136; G06T 7/10; G06T 7/11; G06T 2207/30242;
(Continued)

(56) References Cited

U.S. PATENT DOCUMENTS 5,935,076 A 8/1999 Smith et al.
6,033,076 A * 3/2000 Braeuning ............. A61B 3/024
351/224

(Continued)

FOREIGN PATENT DOCUMENTS

WO WO 9617545 A1 * 6/1996 ............. A61B 3/145
WO WO-2002/015818 A2 2/2002
(Continued)

OTHER PUBLICATIONS

International Search Report for PCT/IB2014/062204, ISA/AU, Woden ACT, dated Aug. 19, 2014.
(Continued)

*Primary Examiner* — Jon Chang
(74) *Attorney, Agent, or Firm* — Harness, Dickey & Pierce, P.L.C.

(57) ABSTRACT

A system for use in remote medical diagnosis of a biological subject, the system including one or more electronic processing devices that receive image data indicative of at least one image of part of the subject's eye from a client device via a communications network, review subject data indicative of at least one subject attribute, select at least one analysis process using results of the review of the subject data, use the analysis process to quantify at least one feature in the image data and generate an indicator value indicative (Continued)

US 9,898,659 B2

Page 2

19 Claims, 13 Drawing Sheets

(51) Int. Cl.
GO6T 7/00 (2017.01)
H04N 7/15 (2006.01)
H04N 5/44 (2011.01)
GO6T 7/10 (2017.01)
GO6T 7/11 (2017.01)
GO6T 7/136 (2017.01)
A61B 3/00 (2006.01)
A61B 3/12 (2006.01)
GO6F 19/00 (2018.01)

(52) U.S. Cl.
CPC ..... G06F 19/3443 (2013.01); G06K 9/00604 (2013.01); G06K 9/6201 (2013.01); G06T 7/0012 (2013.01); G06T 7/10 (2017.01); G06T 7/11 (2017.01); G06T 7/136 (2017.01); H04N 5/44 (2013.01); H04N 7/15 (2013.01); A61B 3/0025 (2013.01); A61B 3/12 (2013.01); G06F 19/321 (2013.01); G06T 2207/20112 (2013.01); G06T 2207/30041 (2013.01); G06T 2207/30168 (2013.01); G06T 2207/30242 (2013.01)

(58) Field of Classification Search
CPC . G06T 2207/30168; G06T 2207/20112; G06T 2207/30041; G06F 19/328; G06F 19/3443; G06F 19/345; G06F 19/321; H04N 7/15; H04N 5/44; G06K 9/0061; G06K 9/00604; G06K 9/6201; A61B 3/0025; A61B 3/12
See application file for complete search history.

(56) References Cited

U.S. PATENT DOCUMENTS

| 6,305,804 | B1 | 10/2001 | Rice et al. | |
|---|---|---|---|---|
| 7,283,653 | B2 | 10/2007 | Zahlmann et al. | |
| 8,793,142 | B2* | 7/2014 | Fishman | G06Q 50/22 600/300 |
| 2002/0052551 | A1 | 5/2002 | Sinclair et al. | |
| 2003/0117580 | A1* | 6/2003 | Franz | A61B 3/0058 351/205 |
| 2004/0102682 | A1 | 5/2004 | Zahlmann et al. | |
| 2004/0220464 | A1 | 11/2004 | Benninger et al. | |
| 2011/0085138 | A1* | 4/2011 | Filar | A61B 3/12 351/206 |
| 2011/0242306 | A1* | 10/2011 | Bressler | A61B 3/12 348/78 |
| 2012/0177262 | A1 | 7/2012 | Bhuiyan | |
| 2016/0166141 | A1 | 6/2016 | Kanagasingam et al. | |

FOREIGN PATENT DOCUMENTS

| WO | WO-2004/049185 A1 | 6/2004 |
|---|---|---|
| WO | WO 2011/022783 | 3/2011 |
| WO | WO-2013/061050 A1 | 5/2013 |

OTHER PUBLICATIONS

International Search Report and Written Opinion of the ISA for PCT/AU2014/050043, ISA/AU, Woden ACT, dated Aug. 19, 2014.
Kaushik S, Tan AG, Mitchell P, Wang JJ, "Prevalence and associations of enhanced retinal arteriolar light reflex: a new look at an old sign", Ophthalmology 2007, 114(1):113-120.
Liew G, Sharrett AR, Kronmal R, Klein R, Wong TY, Mitchell P, Kifley A, Wang JJ, "Measurement of Retinal Vascular Caliber: Issues and Alternatives to Using the Arteriole to Venule Ratio", Investigative Ophthalmology and Visual Science 2007, 48(1):52-57.
J. Canny, "A computational approach to edge detection," IEEE Trans. Pattern Analysis and Machine Intelligence, vol. 8(6), pp. 679-698, 1986.
L. Huiqi, W. Hsu, M. L. Lee, and T. Y. Wong, "Automatic grading of retinal vessel caliber", IEEE Transactions on Biomedical Engineering, vol. 52, pp. 1352-1355, 2005.
Narasimha-Iyer, H, Mahadevan, V., Beach, J. M., Roysam, B., "Improved Detection of the Central Reflex in Retinal Vessels Using a Generalized Dual-Gaussian Model and Robust Hypothesis Testing", IEEE Transactions on Information Technology in Biomedicine 2008, 12(3): 406-410.
Hubbard LD, Brothers RJ, King WN, Clegg LX, Klein R, Cooper LS, Sharrett AR, Davis MD, Cai J, "Methods for evaluation of retinal microvascular abnormalities associated with hypertension/sclerosis in the Atherosclerosis Risk in Communities Study", Ophthalmology, 106, 2269-2280, 1999.
Knudtson MD, Lee KE, Hubbard LD, Wong TY, Klein R, Klein BE, "Revised formulas for summarizing retinal vessel diameters", Current Eye Research, vol. 27, No. 3, pp. 143-149, 2003.
Mainster MA, "The fractal properties of retinal vessels: embryological and clinical implications", Eye (1990) 4, 235-241.
Hart WE, Goldbaum M, Cote B, Kube P, Nelson MR, "Measurement and classification of retinal vascular tortuosity", International Journal of Medical Informatics 53 (1999), 239-252.
Chapman N, Dell'omo G, Sartini MS, Witt N, Hughes A, Thom S, Pedrinelli R, "Peripheral vascular disease is associated with abnormal arteriolar diameter relationships at bifurcations in the human retina", Clinical Science (2002), 103, 111-116.
King LA, Stanton AV, Sever PS, Thom SA, Hughes AD, "Arteriolar length-diameter (L:D) ratio: A geometric parameter of the retinal vasculature diagnostic of hypertension", Journal of Human Hypertension (1996) 10, 417-418.
S Frost, Y Kanagasingam, H Sohrabi, J Vignarajan, P Bourgeat, O Salvado, V Villemagne, CC Rowe, S Lance Macaulay, C Szoeke, KA Ellis, D Ames, CL Masters, S Rainey-Smith, RN Martins and the AIBL Research Group, "Retinal vascular biomarkers for early detection and monitoring of Alzheimer's disease", Transl Psychiatry (Feb. 26, 2013) 3, e233.
Frost S, Martins RN, & Kanagasingam Y, "Retinal Screening for Early Detection of Alzheimer's Disease", Digital Teleretinal Screening, Teleophthalmology in Practice, Springer 2012, pp. 91-100.
Frost S, Martins RN, Kanagasingam Y, "Ocular Biomarkers for Early Detection of Alzheimer's Disease," Journal of Alzheimer's Disease (2010), vol. 22, pp. 1-16.
Di Xiao, Janardhan Vignarajan, Jane Lock, Shaun Frost, Mei-Ling Tay-Kearney, Yogesan Kanagasingam, "Retinal image registration and comparison for clinical decision support," Australasian Medical Journal, 5(9):507-512, 2012.
Di Xiao, Shaun Frost, Janardhan Vignarajan, Jane Lock, Mei-Ling Tay-Kearney, Yogesan Kanagasingam, "Retinal image enhancement and registration for the evaluation of longitudinal changes", Proc. of SPIE, Medical Imaging 2012, Computer-Aided Diagnosis, vol. 8315, 83152O.
Di Xiao, Jane Lock, Javier Moreno Manresa, Janardhan Vignarajan, Mei-Ling Tay-Kearney, Yogesan Kanagasingam, "Region-based multi-step optic disk and cup segmentation from color fundus image," Proc. of SPIE, vol. 8670, Medical Imaging Feb. 2013.
"Saving eyesight an award-winning ICT endeavour" news article dated Aug. 8, 2011, https://web.archive.org/web/20121019083027/http://www.csiro.au/en/Portals/Media/Saving-eyesight-award-winningendeavour.aspx.
"CSIRO's remote eye screening technology saves sight in rural areas" news article dated Aug. 8, 2011, https://web.archive.org/web/

(56) References Cited

OTHER PUBLICATIONS

20120423013841/http://www.electronicsnews.com.au/features/csiro-s-remote-eye-screening-technology-saves-sigh.
"Award opens eyes to Remote-I" news article dated Dec. 6, 2011, http://www.pulseitmagazine.com.au/index.php?option=com_content&view=article&id=793:award-opens-eyes-to-remotei&catid=16:australian-ehealth&Itemid=328.
"Eyesight-saving technologies wins at Australia's 2011 iAwards" news article dated Aug. 15, 2011, http://www.asianscientist.com/tech-pharma/australia-iawards-2011-remote-i-csiro/.
T. P. Karnowski, Y. Li, L. Giancardo, D. Aykac, K. W. Tobin, E. Chaum, "Automated Image Analysis and the Application of Diagnostic Algorithms in an Ocular Telehealth Network," Digital Teleretinal Screening, 43-57, Springer Berlin Heidelberg, 2012.
A. D. Fleming, K. Goatman, S. Philip, G. J. Prescott, P. F. Sharp, John A Olson, "Automated grading for diabetic retinopathy: a large-scale audit using arbitration by clinical experts," The British Journal of Ophthalmology, 94:1606-1610, 2010.
J. Cunha-Vaz, R. Bernardes, T. Santos, C. Oliveira, C. Lobo, I. Pires, L. Ribeiro, "Computer-aided detection of diabetic retinopathy progression", Digital Teleretinal screening, 59-66, Springer Berlin Heidelberg, 2012.
Delori, F. C. "Noninvasive Technique for Oximetry of Blood in Retinal Vessels", Applied Optics; Mar. 15, 1988, vol. 27, No. 6; pp. 1113-1125.
Bankhead P et al., "Fast Retinal Vessel Detection and Measurement Using Wavelets and Edge Location Refinement", PLOS One (2012), vol. 7, No. 3, Mar. 2012.
Shin Yeu Ong et al., "Visual Impairment, Age-related Eye Diseases and Cognitive Function, The Singapore Malay Eye Study", Arch Ophthalmol/vol. 130 (No. 7), Jul. 2012.
Mohammad Kamran Ikram et al., "Retinal pathology as a biomarker for cognitive impairment and Alzheimer's disease", J Neurol Neurosurg Psychiatry 2012; 83:917-922.

* cited by examiner

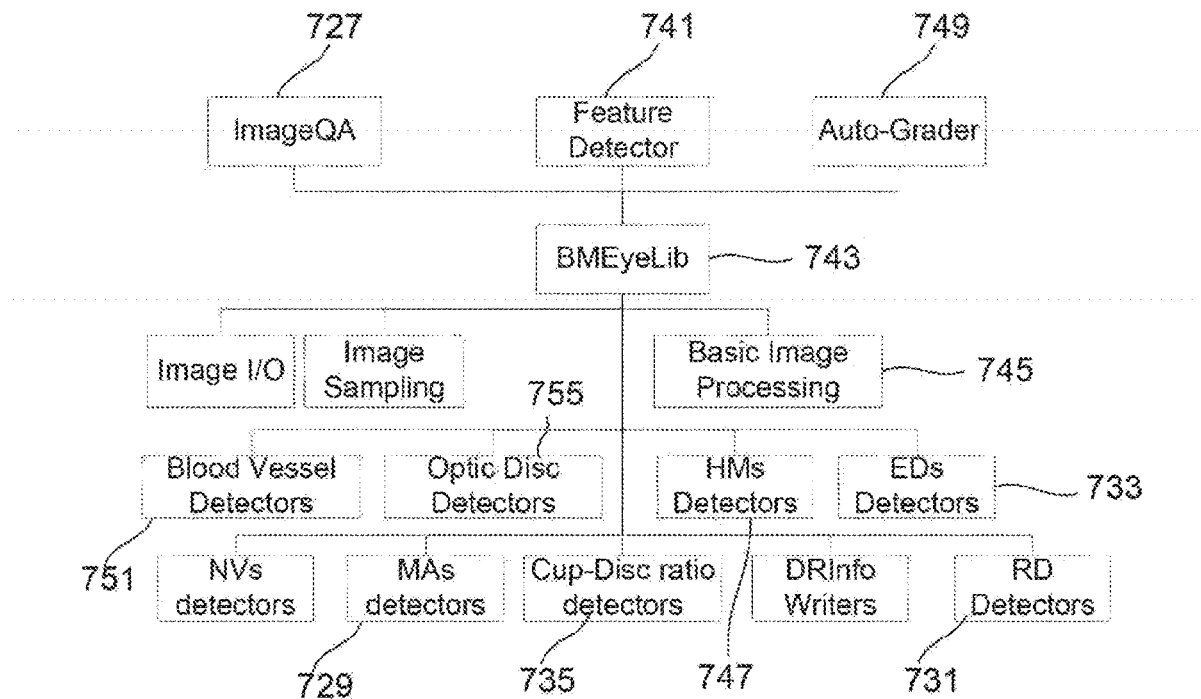
Fig. 7
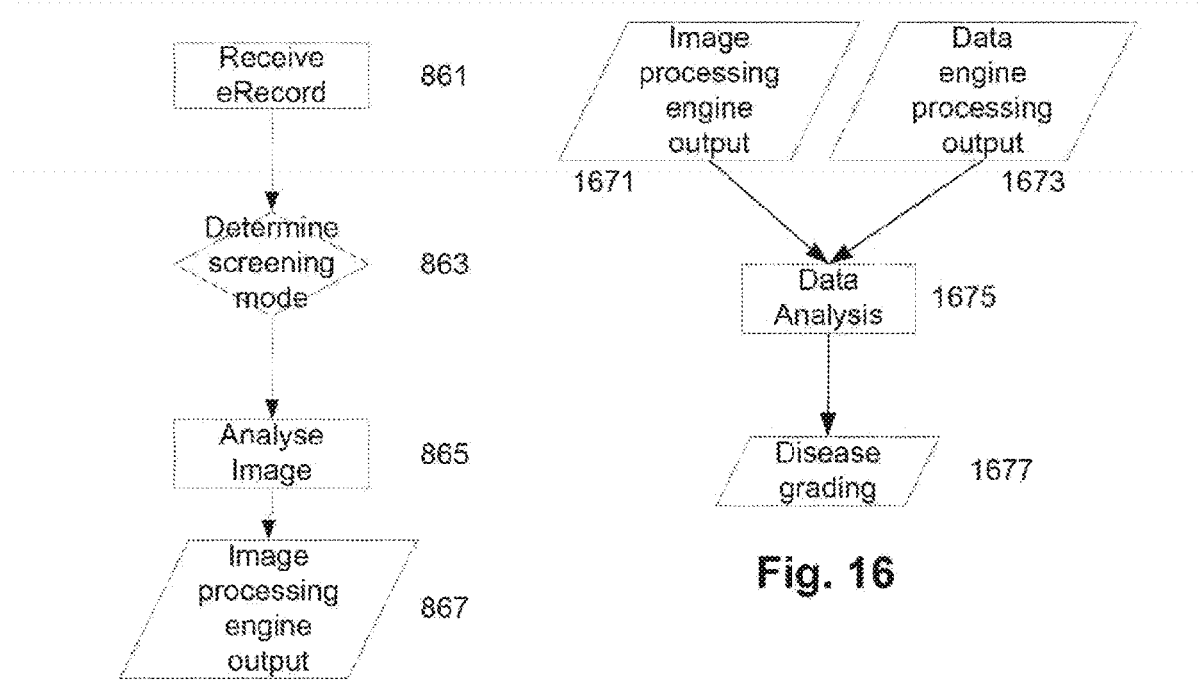
Fig. 8
Fig. 16

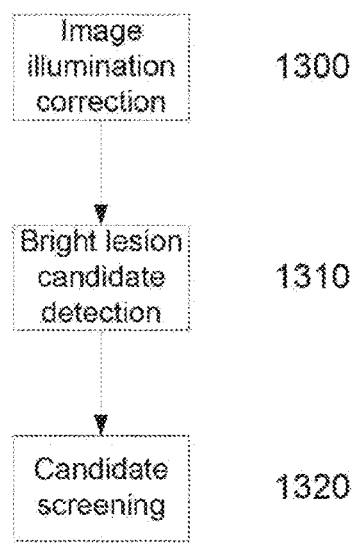
Fig. 13
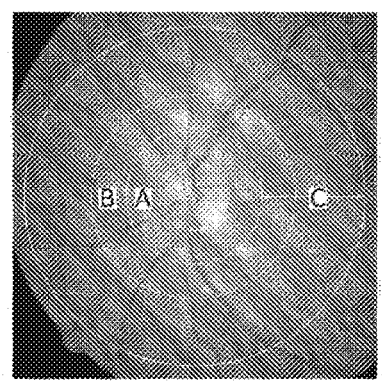
Fig. 14
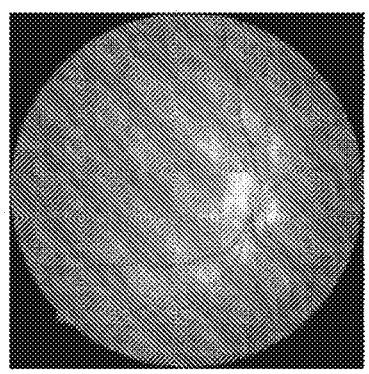 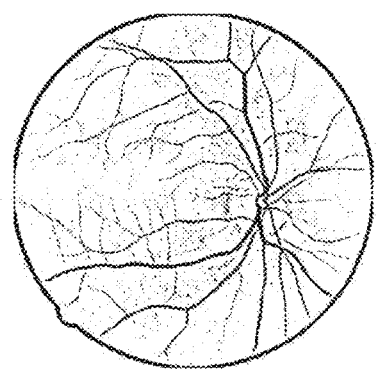
Fig. 15A             Fig. 15B

SYSTEM AND METHOD FOR REMOTE MEDICAL DIAGNOSIS

CROSS-REFERENCE TO RELATED APPLICATIONS

This application is a 371 U.S. National Stage of International Application No. PCT/AU2014/050043, filed May 19, 2014, which claims the benefit of and priority to Australian Patent Application No. 2013901768, filed May 19, 2013. The disclosures of the above applications are incorporated herein by reference.

BACKGROUND OF THE INVENTION

This invention relates to a system for medical diagnosis and support services to consumers over network infrastructure using servers or cloud systems that can be accessed by various clients and a method for providing same.

The invention has particular application with cloud based remote health service delivery that is capable of providing automated clinical decision support based on retinal image analysis and machine learning, and hybrid communication modalities such as video conferencing and store and forward data interactions to deliver health services across a network such as the Internet.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Telehealth has been an evolving technology that has been seen as a convenient and cost effective platform to deliver highly specialised health services to remote locations around the world. With the ubiquity of the Internet and the rapid expansion of cloud based computing services, there is now the ability to provide far more powerful telemedicine services to consumers around the world.

This has resulted in sophisticated communication modalities being developed and adapted to suit the new cloud based computing environment.

SUMMARY OF THE PRESENT INVENTION

In one form the invention seeks to provide a system for use in remote medical diagnosis of a biological subject, the system including one or more electronic processing devices that:
  receive image data indicative of at least one image of part of the subject's eye from a client device via a communications network;
  b) review subject data indicative of at least one subject attribute;
  c) select at least one analysis process using results of the review of the subject data;
  d) uses the analysis process to quantify at least one feature in the image data and
  e) generate an indicator value indicative of the quantified at least one feature, the indicator value being used in the assessment of a condition status of at least one condition.

Typically the one or more electronic processing devices:
  a) analyse the image data to identify at least one type of feature; and
  b) quantify a number of incidences of the at least one type of feature.

Typically the one or more electronic processing devices:
  a) segment the image of at least part of the eye; and,
  b) quantify a number of incidences of the at least one type of feature in each segment of the image.

Typically the one or more electronic processing devices:
  a) compare the indicator value to at least one threshold; and,
  b) generate a notification in accordance with the results of the comparison.

Typically the threshold is at least partially based on at least one of:
  a) at least one previous indicator value for the subject; and,
  b) indicator values measured for a reference population.

Typically the notification is at least one of:
  a) indicative of a condition status;
  b) a referral requirement; and,
  c) used at least in part to initiate a video conference between the client device and a specialist device.

Typically the one or more processing devices transfer an indication of at least one of the indicator value and a notification to the client device for display.

Typically the client device includes:
  a) an imaging device that captures an image of at least part of the eye of the subject; and,
  b) at least one computing system in communication with the imaging device that transfers image data to the one or more electronic processing devices.

Typically the one or more processing devices:
  a) perform image quality assessment; and,
  b) selective analyse the image in accordance with the results of the quality assessment.

Typically the image data is indicative of at least one of:
  a) at least one colour fundus image; and,
  b) an image sequence showing pupil response.

Typically the condition status is at least one of a presence, absence, degree or prognosis of a condition.

Typically the system includes at least one store that stores a number of analysis processes for different screening conditions and wherein the one or more electronic processing devices:
  a) review the subject data to determine at least one screening condition; and,
  b) select at least one analysis process from the number of stored analysis processes in accordance with the at least one screening condition.

Typically the subject data includes an indication of at least one of:
  a) at least one behavioral attribute;
  b) at least one phenotypic attribute;
  c) at least one genetic attribute;
  d) at least one medical intervention;
  e) at least one previous condition;
  f) at least one previous indicator value; and,
  g) part of a medical record.

Typically the features include at least one of:
  a) microaneurysms;
  b) haemorrhages;
  c) lesions; and,
  d) retinal vessel features.

Typically the indicator value is indicative of at least one of:
a) optic disc atrophy;
b) a number of lesions;
c) a number of detached microaneurysms;
d) a number of detached haemorrhages; and,
e) vessel abnormalities.

Typically the image analysis is performed at least in part using a machine learning algorithm.

Typically the one or more processing devices perform image quality assessment by:
a) determining a retinal region mask from the image data;
b) performing image illumination correction to correct for uneven image illumination;
c) detecting bright reflection regions;
d) determining blood vessel distribution;
e) detecting image histogram of the whole retinal region and sub-regions using the region mask; and,
f) performing image quality assessment by evaluating at least one of:
  i) the retinal region mask;
  ii) bright reflection regions;
  iii) whole retinal region histogram;
  iv) sub-region histograms; and,
  v) blood vessel distribution.

Typically the one or more processing devices identify blood vessels by:
a) enhancing the image using linear structuring element processing;
b) detecting blood vessel masks based on associated blood vessel detecting thresholds; and,
c) calculating blood vessel distribution in sub-regions of the image.

Typically the one or more processing devices perform microaneurysm detection by:
a) detecting candidate features in the image; and,
b) selectively excluding candidate features in accordance with at least one of:
  i) candidate feature size; and,
  ii) candidate feature location; and,
c) identifying microaneurysms at least partially in accordance with remaining candidate features.

Typically the one or more processing devices detect candidate features in accordance with pixel parameters of image pixels.

Typically the one or more processing devices determine candidate feature boundaries using region growing.

Typically the one or more processing devices aggregate candidate features with candidate features from a haemorrhage detection process.

Typically the one or more processing devices identify microaneurysms using at least one of:
a) a rule based selection of candidate features; and,
b) a machine learning algorithm.

Typically the one or more processing devices identify microaneurysms using at least one of:
a) candidate feature attributes including at least one of:
  i) compactness;
  ii) contrast;
  iii) pixel hue, saturation or intensity;
  iv) shape;
  v) size; and,
b) connection to blood vessels;

Typically the one or more processing devices perform at least one of:
a) image normalization; and,
b) image illumination correction.

Typically the one or more processing devices perform haemorrhage detection by:
a) detecting candidate features in the image; and,
b) selectively excluding candidate features in accordance with at least one of:
  i) candidate feature size; and,
  ii) candidate feature shape; and,
c) identifying haemorrhages at least partially in accordance with remaining candidate features.

Typically the one or more processing devices detect candidate features by:
a) increasing image contrast; and,
b) comparing image pixel parameters to threshold values.

Typically the one or more processing devices aggregate candidate features with candidate features from a microaneurysm detection process.

Typically the one or more processing devices identify haemorrhages using at least one of:
a) a rule based selection of candidate features; and,
b) a machine learning algorithm.

Typically the one or more processing devices perform retinal optic disc and cup detection by:
a) determining an optic disc location in the image;
b) removing blood vessels from the optic disc region by in-painting;
c) detecting an optic disc region;
d) detecting an optic disc atrophy region;
e) comparing the optic disc region and optic disc atrophy region to determine a true optic disc region; and,
f) performing optic cup detection.

Typically the one or more processing devices detect the optic disc atrophy region using at least one of:
a) texture feature detection;
b) image colour information; and,
c) machine learning using one or more optic disc attributes.

Typically the one or more processing devices use the true optic disc region and optic cup to determine at least one of:
a) a cup-disk ratio; and,
b) peripapillary atrophy.

Typically the one or more processing devices perform bright lesion detection by:
a) detecting candidate features in the image; and,
b) selectively excluding candidate features in an optic disc region.

Typically the one or more processing devices perform blood vessel abnormality analysis by:
a) tracking blood vessels according to at least one of intensity and gradient information;
b) measuring the blood vessel caliber,
c) extracting related features; and,
d) detecting abnormalities in accordance with at least one of the blood vessel caliber and extracted related features.

Typically the one or more processing devices determine an indicator value used in the diagnosis of at least one of:
a) Glaucoma;
b) Age Related Macular degeneration;
c) diabetic retinopathy;
d) Alzheimer's disease;
e) stroke;
f) hypertension; and,
g) cardio vascular disease.

Typically the client device includes a datastore and wherein the client device:
a) generates a record including at least one of:
  i) the image data;
  ii) a subject identifier; and,
  iii) subject data;

b) encrypts the record;
c) stores the encrypted record in the datastore; and,
d) transfers the encrypted record to the one or more processing devices.

Typically the client device stores the encrypted record in the event the communications network is unavailable and transfers the encrypted record to the one or more processing devices once the communications network is available.

In one form the invention seeks to provide a method for use in remote medical diagnosis of a biological subject, the method including, in one or more electronic processing devices:
 a) receiving image data indicative of at least one image of part of the subject's eye from a client device via a communications network;
 b) reviewing subject data indicative of at least one subject attribute;
 c) selecting at least one analysis process using results of the review of the subject data;
 d) using the analysis process to quantify at least one feature in the image data; and,
 e) generating an indicator value indicative of the quantified at least one feature, the indicator value being used in the assessment of a condition status of at least one condition.

In one form the invention seeks to provide a system for use in medical diagnosis of a biological subject, the system including one or more electronic processing devices that:
 a) determine image data indicative of at least one image of part of the subject's eye;
 b) uses at least one analysis process to quantify at least one feature in the image data; and,
 c) generate an indicator value indicative of the quantified at least one feature, the indicator value being used in the assessment of a condition status of at least one condition.

In one form the invention seeks to provide a method for use in medical diagnosis of a biological subject, the method including, in one or more electronic processing devices:
 a) determining image data indicative of at least one image of part of the subject's eye;
 b) using at least one analysis process to quantify at least one feature in the image data; and,
 c) generating an indicator value indicative of the quantified at least one feature, the indicator value being used in the assessment of a condition status of at least one condition.

In one form the invention seeks to provide a system for providing medical diagnosis and support services to consumers over a network using a server infrastructure including:
 a) an image processing and machine learning engine hosting a plurality of imaging and machine learning algorithms having specific execution styles for different disease conditions for deployment by the image processing engine;
 b) a data store engine including a database management system for accessing and managing a data store for selectively storing data and rapidly retrieving same;
 c) a decision support engine for communicating with the image processing and machine learning engine and data store engine to allow decision making on a patient to be performed using data stored in the data store and output from the image processing and machine learning engine;
 d) the decision support engine including a decision making process that performs the following functions:
  i) database analysis to use stored data to analyse the patient's history and produce specific parameters for analysis;
  ii) image processing analysis to produce a quantitative outcome based on the output of the image processing engine; and
  iii) decision orchestration to combine the database analysis and image processing analysis and produce a human readable decision for the patient;
  wherein the image processing and machine learning engine includes: an image quality assessment module, an image feature detection module related to a specific disease screening or diagnosis, and a disease grading module;
  and wherein the decision support engine uses the data stored in the database management system and the data output from the image processing engine to make decisions on a patient by invoking the decision making process to perform the aforementioned functions.

Typically the image processing and machine learning engine uses a hybrid blood vessel and histogram sub-region distribution evaluation algorithm to make image quality assessment of color fundus images.

Typically the image processing and machine learning engine may also be used within an imaging device to provide on the spot advice regarding the image.

Typically the image processing and machine learning engine uses a microaneurysm and haemorrhage detachment algorithm designed to improve the accuracy of microaneurysm and haemorrhage detection.

Typically the image processing and machine learning engine uses a peripapillary atrophy detection method to provide for correct optic disk detection and atrophy detection from fundus images.

Typically the image processing and machine learning engine use a hybrid blood vessel and histogram sub-region distribution evaluation algorithm for color fundus image quality assessment.

Typically the image processing and machine learning engine uses a blood vessel, optic disk, microaneurysm, haemorrhage and bright lesion detection procedure for screening diabetic retinopathy from fundus images.

In one form the invention seeks to provide a method for providing medical diagnosis and support services to consumers over a network including:
 a) performing initial clinical gathering and generating an electronic record of same containing image data to be analysed remotely;
 b) sending the electronic record over the network for diagnosis of a disease condition;
 c) receiving the electronic record and processing and analysing the image data obtained from the initial clinical gathering having regard to one or more disease conditions and providing an image processing output;
 d) retrieving patient history and medical record data previously stored for the patient and producing a data store output; and
 e) receiving the image processing output and the data store output and analysing same to make a final decision on the disease grading in relation to the patient that is human readable.

It will be appreciated that the broad forms of the invention and their respective features can be used in conjunction or interchangeably and reference to separate inventions is not intended to be limiting.

BRIEF DESCRIPTION OF THE DRAWINGS

An example of the present invention will now be described with reference to the accompanying drawings, in which: —

FIG. 7 is a block diagram showing the various functional modules that make up the image processing and machine learning engine;

FIG. 8 is a high level flow chart showing the operation of the image processing engine;

FIG. 13 is a flow chart of an example of a method of retinal optic disc and cup detection;

FIG. 14 is a rendered perspective view of a retinal image showing the optic disc area and the retinal zones;

FIG. 15A is an example of fundus image of an eye;

FIG. 15B is a schematic diagram of an example of a blood vessel mask derived from the image of FIG. 15A;

FIG. 16 is a high level flow chart showing the operation of the design support engine;

DETAILED DESCRIPTION OF THE PREFERRED EMBODIMENTS

Figure 1:
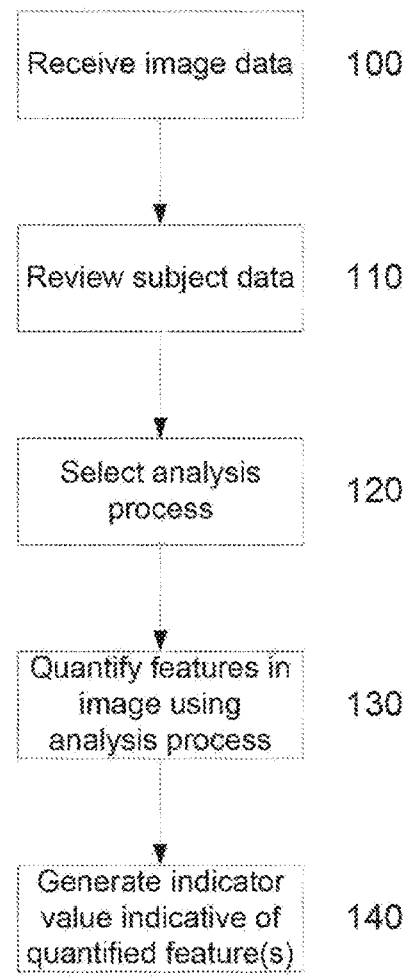
FIG. 1 is a flow chart of an example of a process for use in remote medical diagnosis.

An example of a process for use in remote medical diagnosis of a biological subject will now be described with reference to FIG. 1.

In this example, it is assumed that the process is performed at least in part using an one or more electronic processing devices, for example forming part of a cloud or server based architecture, which are in turn connected to one or more other computing systems or other client devices, via a network architecture, as will be described in more detail below.

In this example, at step 100, the one or more electronic processing devices receive image data indicative of at least one image of part of the subject's eye, and more typically at least part of the subject's retina, from the client device via the communications network. The manner in which this is achieved and the nature of the image will vary depending on the preferred implementation. Typically, the images are retinal images, and in particular fundus images captured using a fundus imaging device connected to a computing system, although alternatively the image data could form part of an image sequence showing pupil response. The images are then typically uploaded to the one or more electronic processing using suitable file transfer techniques.

At step 110, the one or more processing devices review subject data indicative of at least one subject attribute. In this regard, the subject attribute is typically an attribute that can be used to assess conditions for which the subject should be screened. This can therefore include some or all of a subject's medical history, phenotypic information, genetic information, behaviours such as levels of exercise or diet, or the like. The review can be performed in any suitable manner and may include receiving subject data at the same time as the image data or alternatively retrieving the subject data from a store, such as a medical records database or the like.

At step 120 one or more processing devices use this information to select at least one analysis process. In this regard, a number of different analysis processes will typically be provided, each of which can be used in processing the images to screen for a particular condition, such as neuro-degenerative disorders, age-related Macular degeneration, diabetic retinopathy. Rather than use each analysis technique, which would be time consuming and expensive, it is more typical to run one or more selected analyses to screen for particular conditions of interest, as determined based on the review of the subject data.

Following this, at step 130 the one or more processing devices use the analysis process to quantify at least one feature in the image data. Thus, the analysis process could involve performing image analysis to identify microaneurysms, haemorrhages or blood vessels, and then characterise these, for example to and associated parameters, such as dimensions, presence of branching, or the like, or simply to determine the relative abundance.

A step 140 the one or more processing devices use the features to generate an indicator value indicative of the quantified at least one feature. This can be as straightforward as a simple sum of the number of features, or could involve determining more complex indicators, such as ratios of dimensions of different vessels, or the like. This indicator value can then be used in the assessment of a condition status of at least one condition. This can be achieved by displaying an indication of the indicator value to an analyst or operative, for example by returning the indicator value to the client device, or providing this to a specialist, or could alternative involve performing automated interpretation of the value, for example by comparing this to a threshold or the like.

Accordingly, the above described process allows an image of part of a subject's eye to be analysed to allow a status of a condition of the subject, such as the presence, absence, degree or prognosis associated with one or more diseases, to be determined. This process is performed by transferring image data via a communications network, allowing the processing to be performed at a different location to where the image is collected. In particular, this allows to the image to be collected in a remote location, where access to medical facilities may be limited, with the image being transferred to a central location for analysis.

To reduce the analysis burden, which could become undue if a large number of subjects are using the system, the electronic processing device(s) use information regarding the subject, such as a medical history, behavioural, phenotypic or genetic information, to ascertain what conditions should be screened for, carrying out the image analysis on this basis.

A straightforward numerical indicator can then be provided, allowing this to be easily interpreted by an operative with even minimal training, thereby reducing the burden for medical practitioners, and in particular specialists in remote locations. In the event that further more in depth medical review is required, this can then be performed as required, with the system optionally providing telemedicine capabilities, allowing the subject to communicate directly with a specialist via the communications network.

Accordingly, it will be appreciated that the above described process provides a simple mechanism for providing subject with access to screening in remote areas, thereby minimising the risk of serious conditions being overlooked, whilst minimising the burden on the healthcare system.

A number of further features will now be described.

In one example, the one or more electronic processing devices analyse the image data to identify at least one type of feature and quantify a number of incidences of the at least one type of feature. Thus, the analysis process could examine the images for specific types of feature, depending on the condition being screened, and then quantify these particular features. In one example, the one or more electronic processing devices segment the image of at least part of the eye and quantify a number of incidences of the at least one type of feature in each segment of the image. Thus, the quantification could be performed based on a segment or region of the eye in which the features are present, although this is not essential.

The one or more electronic processing devices can compare the indicator value to at least one threshold and then generate a notification in accordance with the results of the comparison. Thus, this could include assessing the number of incidences of a particular feature and if this is high, this can allow the processing devices to alert the subject, an operative or a specialist, allowing a more in depth medical assessment to be performed.

The threshold can be based on a previous indicator value for the subject, so for example the subject could be monitored over a time period to see if the number of microaneurysms or haemorrhages increase. Additionally and/or alternatively this could be based on values measured for a reference population, so absolute threshold values could be established which represent the presence, absence or degree of a condition, based on comparison to data collected from other individuals. The notification can be indicative of a condition status, a referral requirement or used at least in part to initiate a video conference between the client device and a specialist device, so that the subject can have a consultation with a specialist, for example via video conference, as will be appreciated by persons skilled in the art.

In one example, the one or more processing devices transfer an indication of at least one of the indicator value and a notification to the client device for display, although other suitable techniques for communicating results can be used.

The client device typically includes an imaging device that captures an image of at least part of the eye of the subject and at least one computing system in communication with the imaging device that transfers image data to the one or more electronic processing devices. Thus, this could include a fundus camera coupled to a computing system, or the like. It will be appreciated from this that equipment requirements at the client side are minimal and the process can typically be performed in any optometrist premises, allowing this to be widely implemented without significant hardware requirements.

The client device can also include a datastore, which could include an in-built memory, database, remote storage media such as a USB drive, memory card, or the like, with the client device generating a record including the image data, a subject identifier or subject data. The client device can then encrypt the record and store the encrypted record in the datastore allowing this to be transferred to the one or more processing devices as required. Thus, for example, this allows the client device to store the encrypted record in the event the communications network is unavailable and transfers the encrypted record to the one or more processing devices once the communications network is available. This enables the system to be used in an offline mode whilst ensuring privacy and security of the subject and image data is maintained.

The one or more processing devices can perform image quality assessment to ensure that the captured image is of a suitable quality, and then only analyse the image if quality assessment criteria are met. This helps reduce the likelihood of false positive or negative results based on poor quality images. In the event that the images are not of sufficient quality, it will be appreciated that new images could be captured as required.

As mentioned above, the image data is typically indicative of at least one colour fundus image, although other suitable imaging modalities could be used.

In general, the system used to implement the process includes a store, such as a database or the like, that stores a number of analysis processes for different screening conditions and wherein the one or more electronic processing devices review the subject data to determine at least one screening condition and select the at least analysis process from the number of stored analysis processes in accordance with the at least one screening condition. Thus, it will be appreciated that this allows screening to be performed for a wide range of different conditions. Furthermore, by providing access to suitable analysis processes, this allows additional screening techniques to be added at a later date, allowing the scope of the screening to be expanded.

As previously mentioned, the subject data is typically used to determine which conditions should be screened for and this can therefore include a wide range of different data. For example, this could include behavioural attributes, such as levels or exercise, details of diet, smoking history, or the like. This could include phenotypic attributes, including, but not limited to age, gender, ethnicity, or the like, genetic attributes, such as results of genetic screening, presence of identified genetic markers, such as SNPs (Single-Nucleotide Polymorphisms), or the like. The subject data could include information regarding previous medical interventions or conditions, and could therefore be based on or include a medical history. This could also include previous indicator values measured for the subject, allowing a longitudinal study to be performed.

The above described techniques can be applied to a wide range of different features, including but not limited to microaneurysms, haemorrhages, lesions and retinal vessel features, as will be described in more detail below. This can in turn be used to determine a number of different indicator values, including but not limited to an arteriole-to-venule ratio, a branching coefficient, an asymmetry factor, a junctional exponent deviation, a pupillary response time, a vessel reflection index, optic disc atrophy, a number of lesions, a number of detached microaneurysms and a number of detached haemorrhages.

In one example, the one or more processing devices perform image quality assessment by determining a retinal region mask from the image data, performing image illumination correction to correct for uneven image illumination, detecting bright reflection regions, determining blood vessel distribution, detecting image histogram of the whole retinal region and sub-regions using the region mask and performing image quality assessment by evaluating one or more of the retinal region mask, bright reflection regions, whole retinal region histogram, sub-region histograms and blood vessel distribution. Thus, the one or more processing systems can perform preliminary analysis of the image to ensure the image contains expected and/or required features, thereby ensuring the image will be suitable for use in the analysis process. In the event that the image is unsuitable, this allows the image to be recaptured.

The one or more processing devices identify blood vessels by enhancing the image using linear structuring element processing, detecting blood vessel masks based on associated blood vessel detecting thresholds and calculating blood vessel distribution in sub-regions of the image, although any suitable technique could be used.

The one or more processing devices typically perform microaneurysm detection by detecting candidate features in the image and then selectively excluding candidate features in accordance with at least one of candidate feature size and location, allowing the remaining candidate features to be used in identifying microaneurysms. In this regard, candidate features can be determined in accordance with pixel parameters, such as pixel intensity, of image pixels. Following identification of candidate features, the boundaries of these can be determined with greater accuracy using a using region growing.

The candidate features determined using the above process can also be combined with candidate features from a haemorrhage detection process. This increases the number of candidate features that are used in the detection of microaneurysms, which can in turn avoid microaneurysms being overlooked.

The one or more processing devices typically identify microaneurysms from the candidate features using a rule based selection of candidate features or a machine learning algorithm. This can be performed on the basis of candidate feature attributes including, but not limited to any one or more of compactness, contrast, pixel hue, saturation or intensity, shape, size and connection to blood vessels.

The one or more processing systems may also optionally perform image normalization or image illumination correction to optimize the image for subsequent processing.

The one or more processing devices typically perform haemorrhage detection by detecting candidate features in the image, selectively excluding candidate features in accordance with at least one of candidate feature size and candidate feature shape and identifying haemorrhages at least partially in accordance with remaining candidate features. In this regard, the candidate features can be detected by increasing image contrast and comparing image pixel parameters to threshold values. As described above, the candidate features can be aggregated with candidate features from a microaneurysm detection process. The one or more processing devices can identify haemorrhages using a rule based selection of candidate features or a machine learning algorithm.

The one or more processing devices can perform retinal optic disc and cup detection by determining an optic disc location in the image, removing blood vessels from the optic disc region by in-painting, detecting an optic disc region, detecting an optic disc atrophy region, comparing the optic disc region and optic disc atrophy region to determine a true optic disc region and performing optic cup detection. The optic disc atrophy region can be detected using texture feature detection, image colour information or machine learning using one or more optic disc attributes, although other suitable techniques could be used.

The one or more processing devices can use the true optic disc region and optic cup to determine a cup-disk ratio or a degree of peripapillary atrophy, which can for example be used in the diagnosis of glaucoma.

The one or more processing devices can perform bright lesion detection by detecting candidate features in the image and selectively excluding candidate features in an optic disc region.

The techniques could be used to determine an indicator value used in the diagnosis of a variety of conditions including glaucoma, Age Related Macular degeneration, diabetic retinopathy, Alzheimer's disease, stroke, hypertension and cardio vascular disease.

It will further be appreciated that the above described process collects a wide range of image data from a number of different subjects. Through subsequent clinical validation of any diagnoses performed using the image data, this provides a useful training set that can be used in assessing suitable thresholds. Additionally, this can be used as part of a machine learning process, allowing for improvements in the accuracy in detection of features and interpretation of results.

Figure 2:
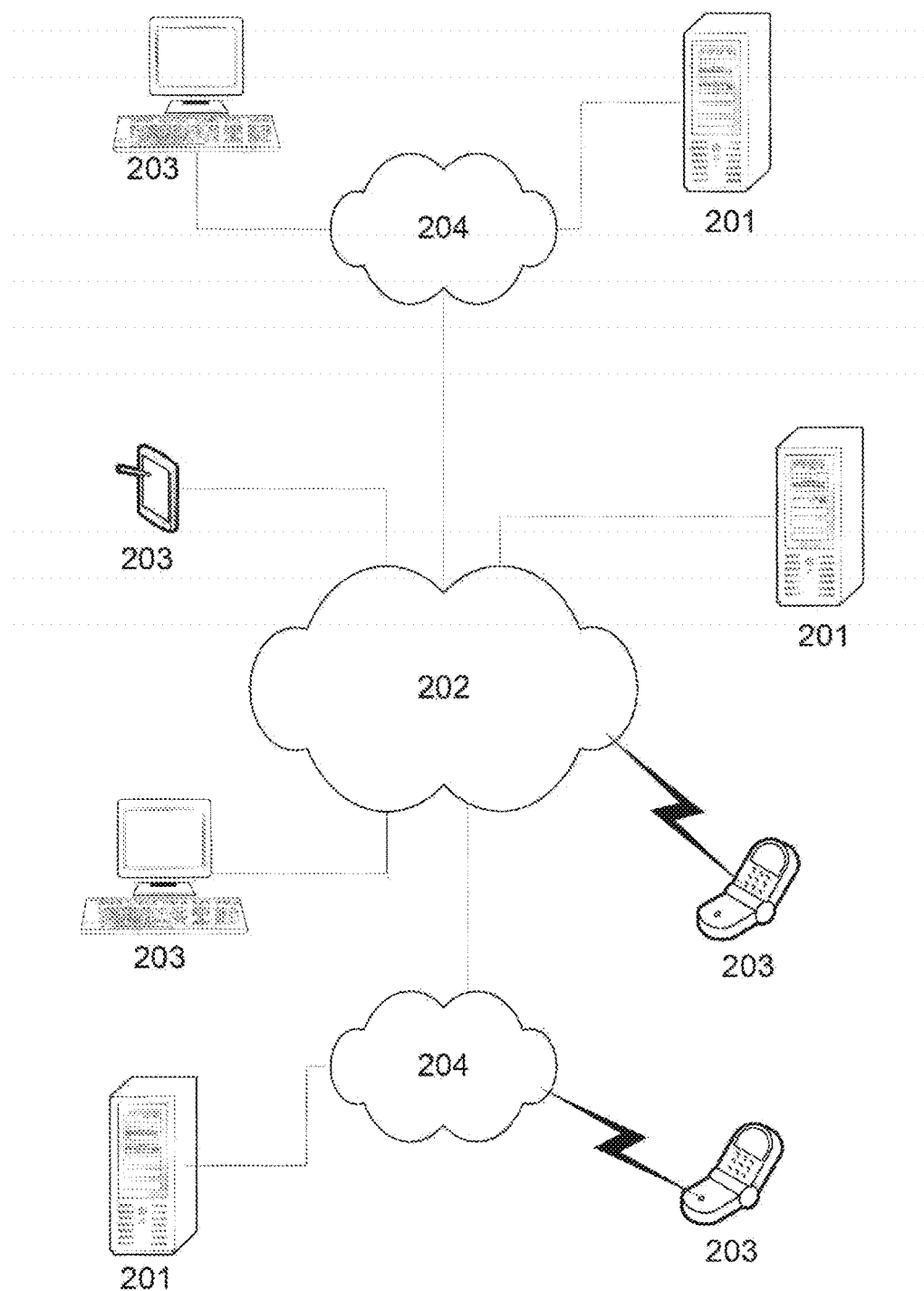
FIG. 2 is a schematic diagram of an example of a distributed computer architecture.

In one example, the process is performed by one or more processing systems operating as part of a distributed architecture, an example of which will now be described with reference to FIG. 2.

In this example, a base station 201 is coupled via a communications network, such as the Internet 202, and/or a number of local area networks (LANs) 204, to a number of computing systems 203. It will be appreciated that the configuration of the networks 202, 204 are for the purpose of example only, and in practice the base station 201 and computing systems 203 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, the base station 201 includes one or more processing systems 210 coupled to a database 211. The base station 201 is adapted to be used in performing the analysis of the image data, including reviewing the subject data, selecting an analysis process and providing results of the analysis. The computing systems 203 are typically adapted to communicate with the base station 201, allowing image and/or subject data to be provided and to allow details of indicator values or notifications to be received. Additionally, the computing systems can be adapted to allow video conferencing to be performed for example to allow for remote consultation with a specialist.

Whilst the base station 201 is a shown as a single entity, it will be appreciated that the base station 201 can be distributed over a number of geographically separate locations, for example by using processing systems 210 and/or databases 211 that are provided as part of a cloud based environment. It will also be appreciated that the above described arrangement is not essential and other suitable configurations could be used.

Figure 3:
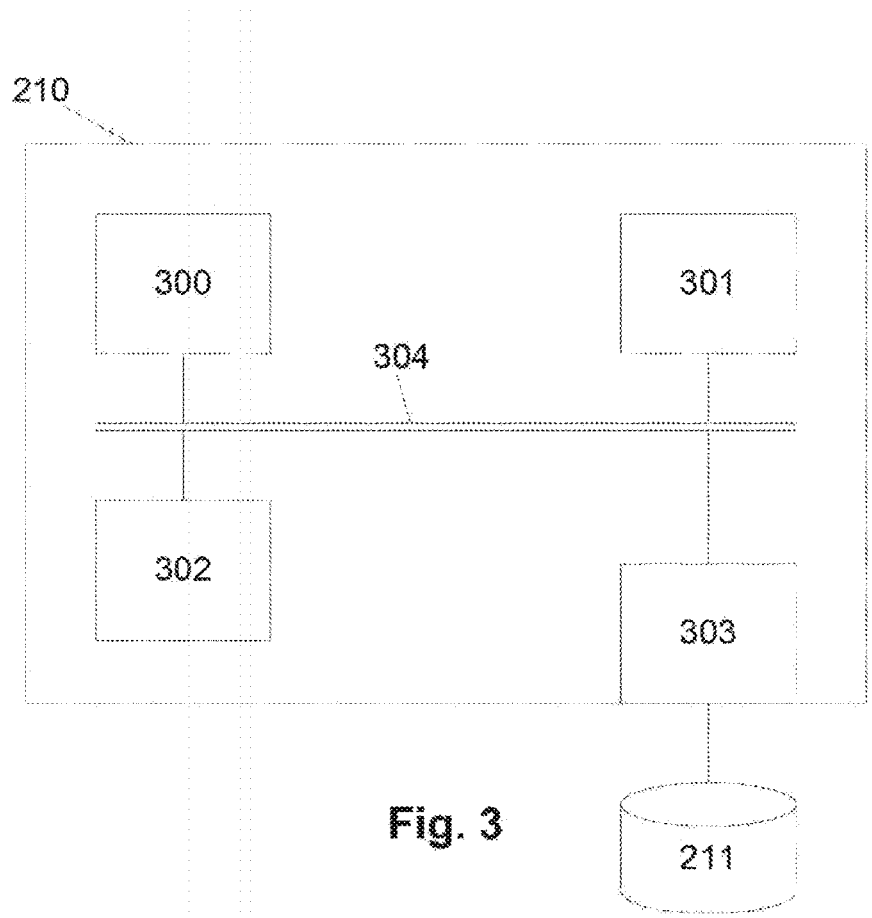
FIG. 3 is a schematic diagram of an example of a processing system of FIG. 2.

An example of a suitable processing system 210 is shown in FIG. 3. In this example, the processing system 210 includes at least one microprocessor 300, a memory 301, an optional input/output device 302, such as a keyboard and/or display, and an external interface 303, interconnected via a bus 304 as shown. In this example the external interface 303 can be utilised for connecting the processing system 210 to peripheral devices, such as the communications networks 202, 204, databases 211, other storage devices, or the like. Although a single external interface 303 is shown, this is for the purpose of example only, and in practice multiple interfaces using various methods (eg. Ethernet, serial, USB, wireless or the like) may be provided.

In use, the microprocessor 300 executes instructions in the form of applications software stored in the memory 301 to allow the analysis process and any other associated tasks to be performed. The applications software may include one or more software modules, and may be executed in a suitable execution environment, such as an operating system environment, or the like, and specific examples will be described in more detail below.

Accordingly, it will be appreciated that the processing system 210 may be formed from any suitable processing system, such as a suitably programmed computer system, PC, web server, network server, or the like. In one particular example, the processing system 210 is a standard processing system such as Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 4:
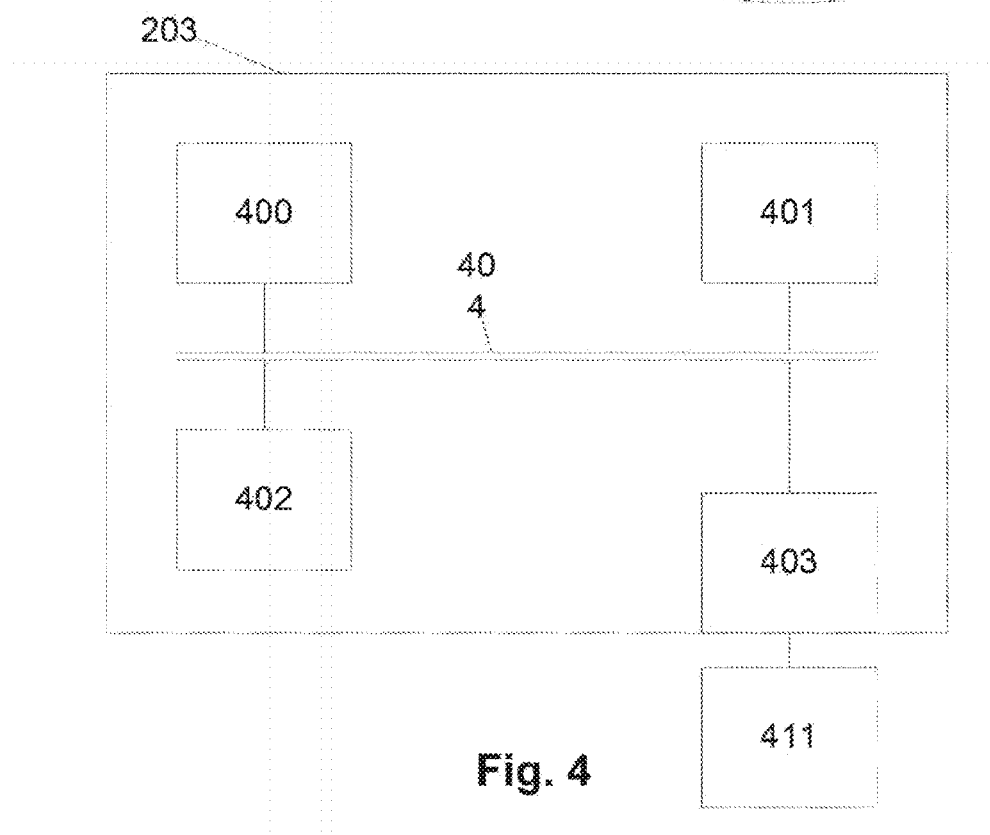
FIG. 4 is a schematic diagram of an example of a computing system of FIG. 2.

As shown in FIG. 4, in one example, the computing system 203 includes at least one microprocessor 400, a memory 401, an input/output device 402, such as a keyboard and/or display, and an external interface 403, interconnected via a bus 404 as shown. In this example the external interface 403 can be utilised for connecting the computing system 203 to peripheral devices, such as the communications networks 202, 204, one or more imaging devices 411, external storage devices, or the like. Although a single external interface 403 is shown, this is for the purpose of example only, and in practice multiple interfaces using various methods (eg. Ethernet, serial, USB, wireless or the like) may be provided.

In use, the microprocessor 400 executes instructions in the form of applications software stored in the memory 401 to allow communication with the base station 201, for example to allow data to be supplied thereto and allowing details of the bidding process to be displayed to participants, such as bidders.

Accordingly, it will be appreciated that the computing systems 203 may be formed from any suitable processing system, such as a suitably programmed PC, Internet terminal, lap-top, hand-held PC, smart phone, PDA, Tablet, web server, or the like. Thus, in one example, the processing system 210 is a standard processing system such as Intel Architecture based processing system, which executes software applications stored on non-volatile (e.g., hard disk) storage, although this is not essential. However, it will also be understood that the computing systems 203 can be any electronic processing device such as a microprocessor, microchip processor, logic gate configuration, firmware optionally associated with implementing logic such as an FPGA (Field Programmable Gate Array), or any other electronic device, system or arrangement.

Further examples of the analysis process will now be described in further detail. For the purpose of these examples, it is assumed that the processing system 210 maintains subject data and databases including analysis techniques and other relevant related information. It is also assumed that the processing system 210 hosts applications software allowing client devices in the form of the computing systems 203 to interact with the processing systems 210, for example to submit image data and receive results of the analysis.

To achieve this the processing system 210 of the base station 201 typically executes applications software, with actions performed by the processing system 210 being performed by the processor 300 in accordance with instructions stored as applications software in the memory 301 and/or input commands received from a user via the I/O device 302, or commands received from the computing system 203.

It will also be assumed that the user interacts with the processing system 210 via a GUI (Graphical User Interface), or the like presented on the computing system 203. Actions performed by the computing system 203 are performed by the processor 401 in accordance with instructions stored as applications software in the memory 402 and/or input commands received from a user via the I/O device 403.

However, it will be appreciated that the above described configuration assumed for the purpose of the following examples is not essential, and numerous other configurations may be used. It will also be appreciated that the partitioning of functionality between the computing systems 203, and the base station 201 may vary, depending on the particular implementation.

Figure 5A:
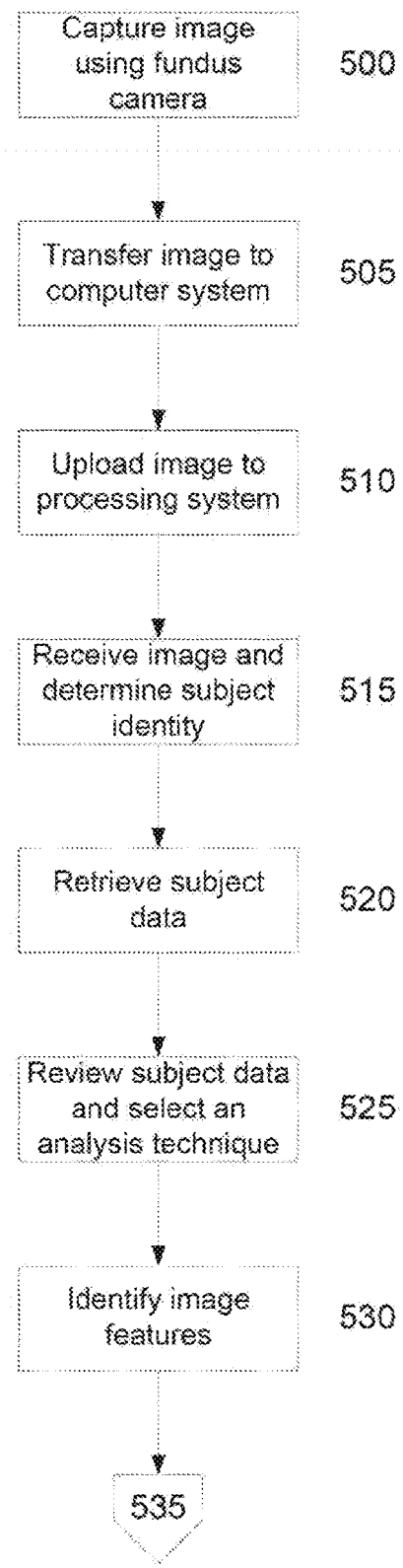
FIGS. 5A and 5B are a flow chart of a second example of a process for use in remote medical diagnosis.
Figure 5B:
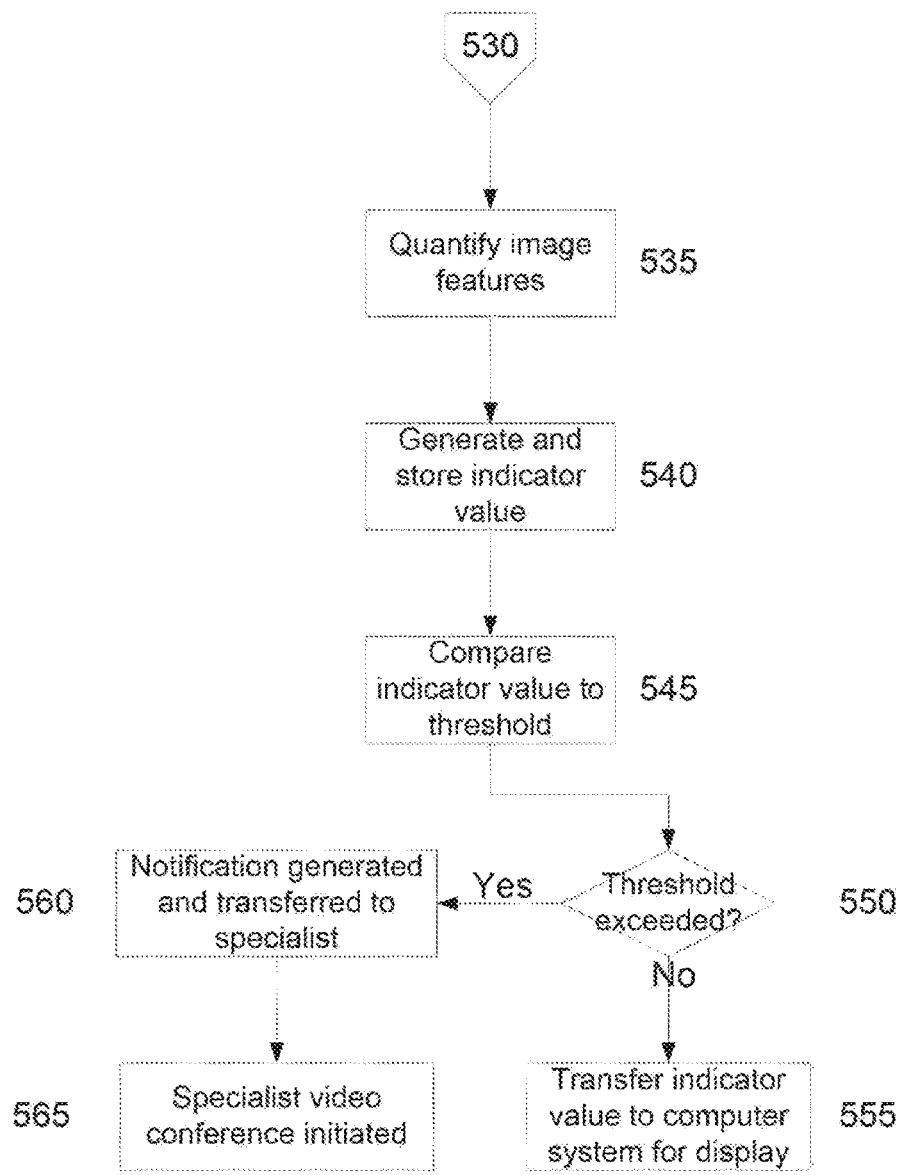

A second example of a method for use in remote diagnosis will now be described with reference to FIGS. 5A and 5B.

In this example, an image capturing device in the form of a fundus camera 411 is used to capture a fundus image of the eye of a subject, with image data then being transferred to the computing system 203 at step 505. At step 510 the computing system transfers image data indicative of the image to the processing system 210. This process may be performed manually, or using a combination of manual and automated processes.

As part of this process, information indicative of an identity of the subject may be transferred to the processing system 210 together with the image data. This can include for example a name and address or a unique identifier such as a medical record number, medicare number, or the like.

At step 515 the processing system 210 receives the image and operates to determine an identity of the subject, for example using the unique identifier or the like. In this regard, the identity of the subject could be anonymised for privacy reasons, in which case the processing system 210 merely determines the unique identifier, as will be appreciated by persons skilled in the art. At step 520 the processing system 210 utilises the subject identity to retrieve subject data, for example, by accessing a medical records database containing a medical record for the subject. If subject data is not available, the processing system 210 may prompt the operator of the computing system 203 to supply the information, for example by requesting this information from the subject and entering this via the computer system 203, as required.

At step 525 the processing system 210 reviews the subject data and uses this to select an analysis technique. This step will typically include performing some form of comparison between the information contained in the medical record and selection criteria, and using the results of the comparison to select a the analysis technique. Thus, for example, this may specify that if the medical record includes specific combinations of attributes, then particular screening techniques could be performed.

At step 530 the processing system 210 operates to identify image features and then quantify these at step 535. The manner in which this is performed will vary depend on the particular analysis techniques selected and an example will be described in more detail below.

At step 540 an indicator value is generated and optionally stored, for example as part of the subject's medical record, with this being compared to a threshold at step 545. The threshold may be of any form and could include a relative threshold, for example based on a previous indicator value determined for the subject, or an absolute threshold, for example based on indicator values measured for a reference population. The threshold can be a single value or a range, for example representing normal indicator values, or indicator value ranges indicative of the presence or degree of a condition.

In the current example, if it is determined that the threshold is not exceeded at step 550, the processing system 210 transfers an indication of the indicator value to the computing system 203 allowing to be displayed to the operator at step 555. This may also include additional information, such as an interpretation of the indicator value, including for example an indication of a presence, absence or degree of a condition. In the event the threshold is exceeded for example if the indicator value falls outside a normal range then a notification can be generated and transferred to a specialist at step 560 via a specialist computing system, allowing a video conference to be initiated at step 565. It will be appreciated that this can be performed in conjunction with provision of the indicator value to the computing system 203, allowing the operator to review this and discuss the result with the subject, prior to the video conference being performed. It will also be appreciated that a range of alternative approaches could be used, such as referring the subject to a specialist in accordance with normal referral techniques.

A number of further features of specific implementations will now be described.

In one specific example, the system includes an image processing and machine learning engine hosting a plurality of imaging algorithms having specific execution styles for different disease conditions for deployment by the image processing and machine learning engine. The image processing and machine learning engine includes an image quality assessment module; an image feature detection module related to a specific disease screening or diagnosis; and, a disease grading module. The system further includes a data store storage engine including a database management system for accessing and managing a data store for selectively storing data and rapidly retrieving same and a decision support engine for communicating with the image processing engine and data store engine to allow decision making on a patient to be performed using data stored in the data store and output from the image processing and machine learning engine. The decision support engine including a decision making process that performs database analysis to use stored data to analyse the patient's history and produce specific parameters for analysis, image processing analysis to produce a quantitative outcome based on the output of the image processing engine and decision orchestration to combine the database analysis and image processing analysis and produce a human readable decision for the patient and wherein the decision support engine uses the data stored in the database management system and the data output from the image processing engine to make decisions on a patient by invoking the decision making process to perform the aforementioned functions.

The image processing and machine learning engine can use a hybrid blood vessel and histogram sub-region distribution evaluation algorithm to make image quality assessment of color fundus images.

The above described image processing and machine learning engine can also be used within an imaging device to provide a stand alone arrangement.

The image processing and machine learning engine can use a microaneurysm and haemorrhage extraction algorithm designed to improve the accuracy of microaneurysm and haemorrhage detection, as well as a peripapillary atrophy detection method to provide for correct optic disk detection and atrophy detection from colour fundus images. The image processing engine can also use a blood vessel, optic disk, microaneurysm, haemorrhage and bright lesion detection procedure for screening diabetic retinopathy from fundus images.

The system can provide medical diagnosis and support services to consumers over a network by performing initial clinical gathering and generating an electronic record of same containing image data to be analysed remotely, sending the electronic record over the network for diagnosis of a disease condition, receiving the electronic record and processing and analysing the image data obtained from the initial clinical gathering having regard to one or more disease conditions and providing an image processing output, retrieving patient history and medical record data previously stored for the patient and producing a data store output and receiving the image processing output and the data store output and analysing same to make a final decision on the disease grading in relation to the patient that is human readable.

In one example, the preferred embodiment is directed towards a cloud based telemedicine system utilising various algorithms for providing medical diagnosis of a patient and support services to a consumer over a network. The network may be a variety of forms: GPRS, 3G, 4G, broadband, satellite, wireless or any other high speed broadband technologies.

The system is structured so that patient screening is performed remotely such as in a rural locality and the medical diagnosis and disease follow-up is performed in a centralized location such as in the metropolitan area of a city, where complex IT hosting and specialist services are more readily available.

The medical diagnosis and disease follow-up locations can also be distributed to several locations such that the system utilises the availability of the specialists effectively.

Figure 6:
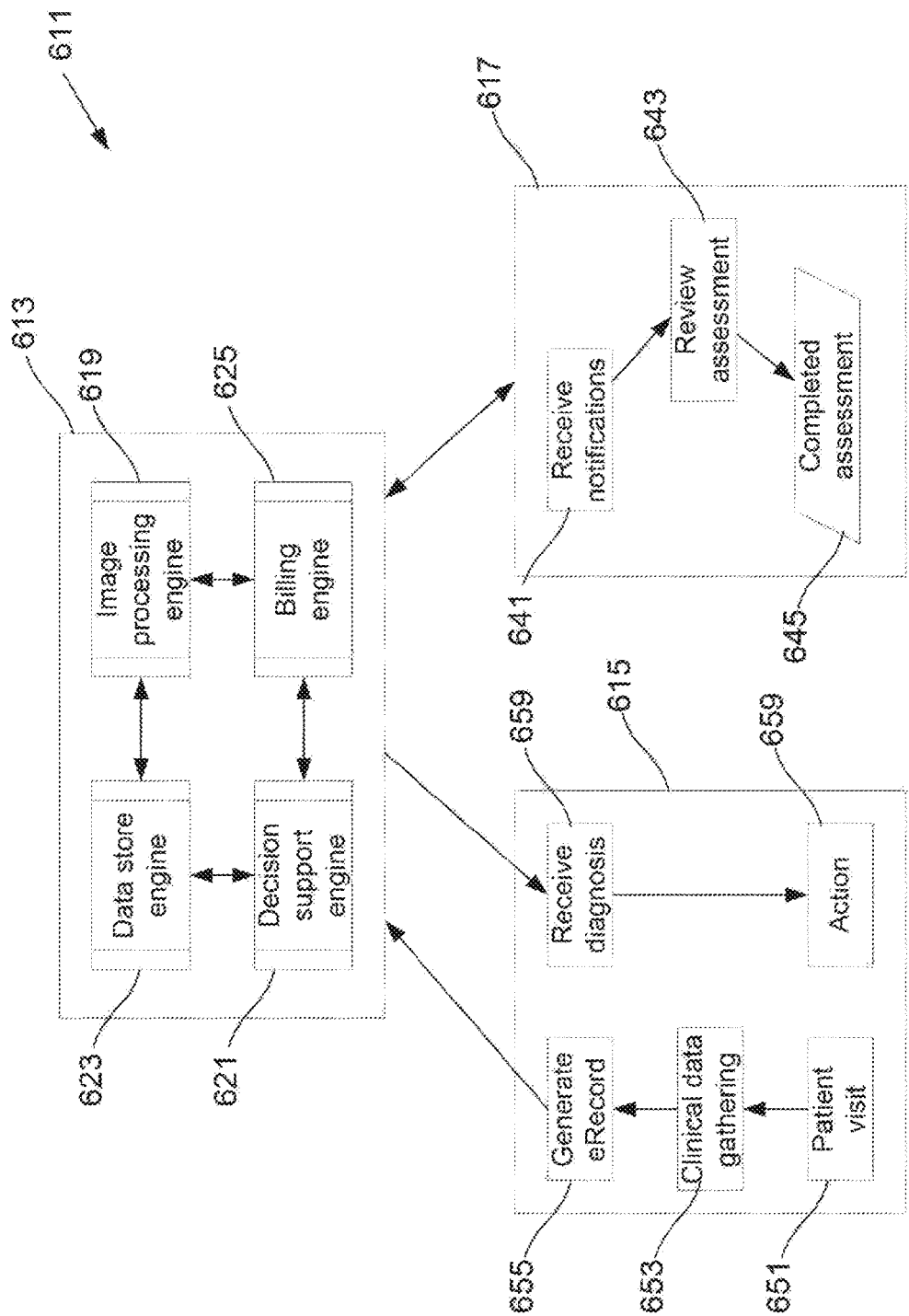
FIG. 6 is a block diagram showing an overview of the system including the cloud based services, the client site and the group of specialists.

The telemedicine system 611 consists of three main components as shown in FIG. 6 of the drawings: a cloud based services component 613, an administrative client site component 615 and a group of specialists component 617 each having their own specialised client application.

The cloud based services component 613 functions as a host or distributed server architecture to the administrative client site 615 and the specialist client application 617. The server (data) host is built using commercial web-server architecture such as Microsoft SQL Server™ to provide a relational database management system and Microsoft IIS™ to provide information services over the Internet. Clearly information technology can change over time and so the invention is not dependent on the particular architecture of the implementation described in the preferred embodiment. For example, it is possible to use PHP™ with MYSQL™ as a server based technology instead.

With the administrative client site 615 and the devices running the specialist client applications 617, standard based web technologies such as web-browser and underlying security (eg: SSL with encryption) are used to communicate with the server host. Similarly, web standards change over time and hence the invention is being adapted to be implemented under different technologies such as HTML5 and Javascript™ or any other languages for structuring and presenting content for the WWW and Internet.

The host server component, as described, utilises cloud based architecture to implement the server side of the telemedicine system. The cloud based architecture serves as a centralised storage solution for medical records and provides advanced decision support services for various disease conditions.

The server consists of various modules. These modules serve different purposes and are categorised into four main sub-components (engines), comprising an image processing and machine learning engine 619, a decision support engine 61, a data store engine 623 and a billing engine 625.

The image processing and machine learning engine 619 hosts various image processing and machine learning algorithms. These algorithms can be proprietary algorithms or open source implementations. They execute in the cloud based servers that comprise the host server and have a certain execution style for different disease conditions. The following are a few examples of different execution algorithms which can be deployed in the image processing engine 619 and are shown as different functional modules in FIG. 7:

a) Medical image quality assessment 727
  i) Retina
  ii) Wounds
  iii) Ultra sound
  iv) Tele-emergency care
  v) OCT Imaging
b) Dental images
c) Retinal microaeneurysms detector 729
d) Retinal Drusen detector for age-related Macular degeneration 731
e) Retinal exudates detector 733
f) Retinal cup-disc detector for glaucoma 735
g) Retinal bio-marker detectors for systematic diseases, e.g. Alzheimer's disease
h) Image registration in BMEyeLib 743.

Some algorithms take high computational resources to process. Thus the host server utilises advanced high-end computing technology to distribute the computations to different nodes of hardware to perform a quicker diagnosis simultaneously.

The basic process adopted by the image processing and machine learning engine 619 as shown in FIG. 8, involves receiving an eRecord of a patient being diagnosed by the system from the data store engine 623 at step 861, determining the particular screening mode required at step 863, analysing the images using the appropriate algorithms for the particular disease condition being screened at step 865 and outputting the results from the image processing engine at step 867.

In the present embodiment, the major functional modules implemented in the image processing engine 619 are retinal image (color fundus image, fluorescein retinal image, OCT image) related feature detection using the feature detector 741 and disease diagnosis using applicable algorithms designed to provide eye disease screening and clinical decision support for eye diseases such as glaucoma, Age Related Macular degeneration and diabetic retinopathy (DR). Other image processing functional modules are used for early detection of Alzheimer's disease, stroke, hypertension, cardio vascular disease and wound care management.

The core function module is BMEyeLib 743, which provides basic image processing algorithms for general retinal image processing 745 and specific algorithms (all detectors) for some specific eye-disease feature detections, including microaneurysm detectors 729 and haemorrhage detectors 747, as shown in FIG. 7.

Based on the functional modules, the image processing and machine learning engine 619 provides three main functions for a complete retinal image processing and analysis: image quality assessment using the ImageQA process 727, image feature detection related to one specific disease screening or diagnosis using the feature detector process 741, and disease grading using the machine learning and auto-grader process 749.

Among these functional modules, the following algorithms, methods and designs are of particular significance in the system: an image quality assessment algorithm, a microaneurysm and haemorrhage detachment algorithm, a peripapillary atrophy detection method, a blood vessel, optic disk, microaneurysm, haemorrhage and bright lesion detection procedure and a method for generating DR, glaucoma and other diseases such as Alzheimer's disease diagnosis and grading information and a formatted dataset.

The image quality assessment algorithm is designed to implement the image quality decision by a hybrid blood vessel and histogram sub-region distribution evaluation approach. The algorithm provides fast retinal blood vessel detection. Image sub-region template is generated based on the detected retinal image area (retinal mask). The image quality is judged based on the rule-based method through analysing the following parameters: the form of the retinal template, the histogram of the pixels in the retinal mask, the blood vessel distribution in the template sub-regions, and the histograms in the template sub-regions. Two-level blood vessel distribution analysis method, which is processing on two blood vessel binary images detected by different threshold settings, is developed for further improving the accuracy of the bad image quality decision.

Figure 9:
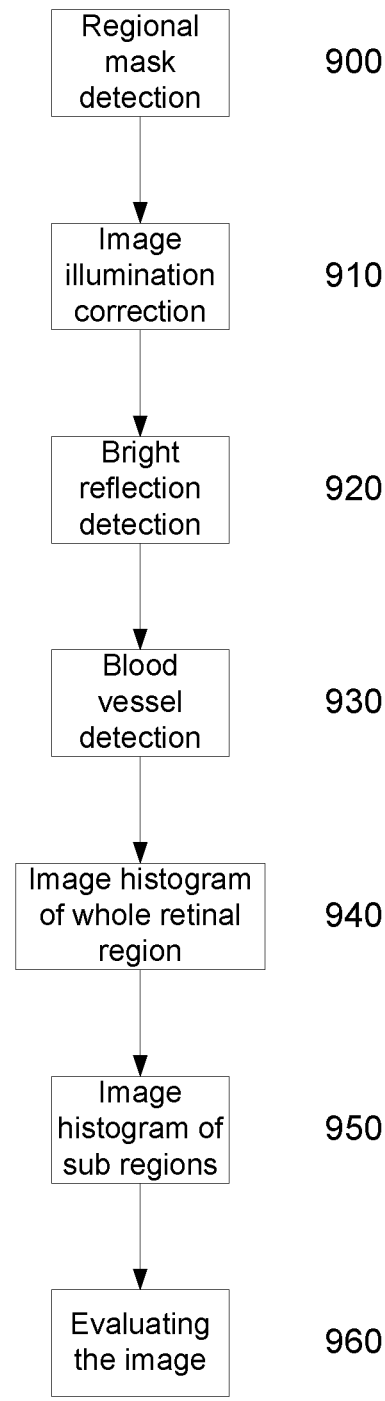
FIG. 9 is a flow chart of an example of a method of image quality assessment.

An example workflow for the image quality assessment will now be described in more detail with reference to FIG. 9.

In this example, at step 900, retinal region mask detection is performed on the original retinal image to identify respective regions of retina. This can be used to segment the retinal image into a number of different regions, with regions being selected either arbitrarily, for example based on size, but is more typically performed based on regions corresponding to features such as the optic disc, or the like. In the current example 12 sub-regions are identified, with these being used in subsequent processing steps. Identification of such region masks is known in the art and will not therefore be described in detail.

At step 910, image illumination correction is performed to correct for uneven illumination of the image and this can be achieved using standard image processing techniques. At step 920, bright reflections are detected, for example based on image pixel parameters, such as the pixel brightness, or the like.

At step 930 blood vessel detection is performed. This can be achieved using any suitable technique, but in one example this is achieved using a linear structuring element (LSE) morphology method. This typically involves performing image enhancement by LSE processing, detecting two blood vessel masks based on two associated blood vessel detecting thresholds and following this calculating blood vessel distribution in 12 sub-regions of the retinal region.

At step 940 an image histogram of the whole retinal region is detected, with image histograms of 12 sub-regions inside the retinal region being determined at step 950.

Image quality assessment is then performed at step 960, on the basis of a number of different rule-based selection criteria. The criteria can vary depending on the preferred implementation, and in one example include:
 a) evaluation of the retinal region mask, for example to ensure all required regions of the retina are present in the image;
 b) Evaluation of the bright reflection regions to ensure there are no excessive reflections that obscure features in the retinal image;
 c) Evaluation of the whole retinal region histogram to ensure that pixel parameters, such as contrast, are distributed across an expected range;
 d) Evaluation of the 12 sub-region histograms to ensure that pixel parameters, such as contrast, are distributed across an expected range. In this regard it will be appreciated that the histograms for different regions, such as the fovea and optic disc will inherently be different due to the different optical properties of these retinal features; and,
 e) Two-level blood vessel distribution analysis on the blood vessel masks to ensure an optimal threshold is selected for blood vessel distribution analysis and to provide the improved accuracy for bad image quality decision.

It will be appreciated that if any of the above criteria are not met, it may not be possible to use the image in the subsequent analysis steps, in which case capturing of the image may need to be repeated. In this instance, a notification can be provided to the operator of the client device, thereby allowing the operator to repeat the image capture process.

The microaneurysm and haemorrhage detachment algorithm is designed to improve the accuracy of microaneurysm and haemorrhage detection. The algorithm aims at detaching the microaneuryms and haemorrhages, which are close to, or attached with, the retinal blood vessels. Conventional blood vessel detection methods usually detect the microaneurysms and haemorrhages as integral parts of blood vessels when they are close to, or attached with, the nearby blood vessels, thereby reducing the positive rate of microaneurysm and haemorrhage detection. The algorithm detects these particular microaneurysms and haemorrhages through analysing the tips of detected blood vessel branches by their areas and analysing the form features of blood vessel medial lines at the branch tips to distinguish them from the normal blood vessels.

Figure 10:
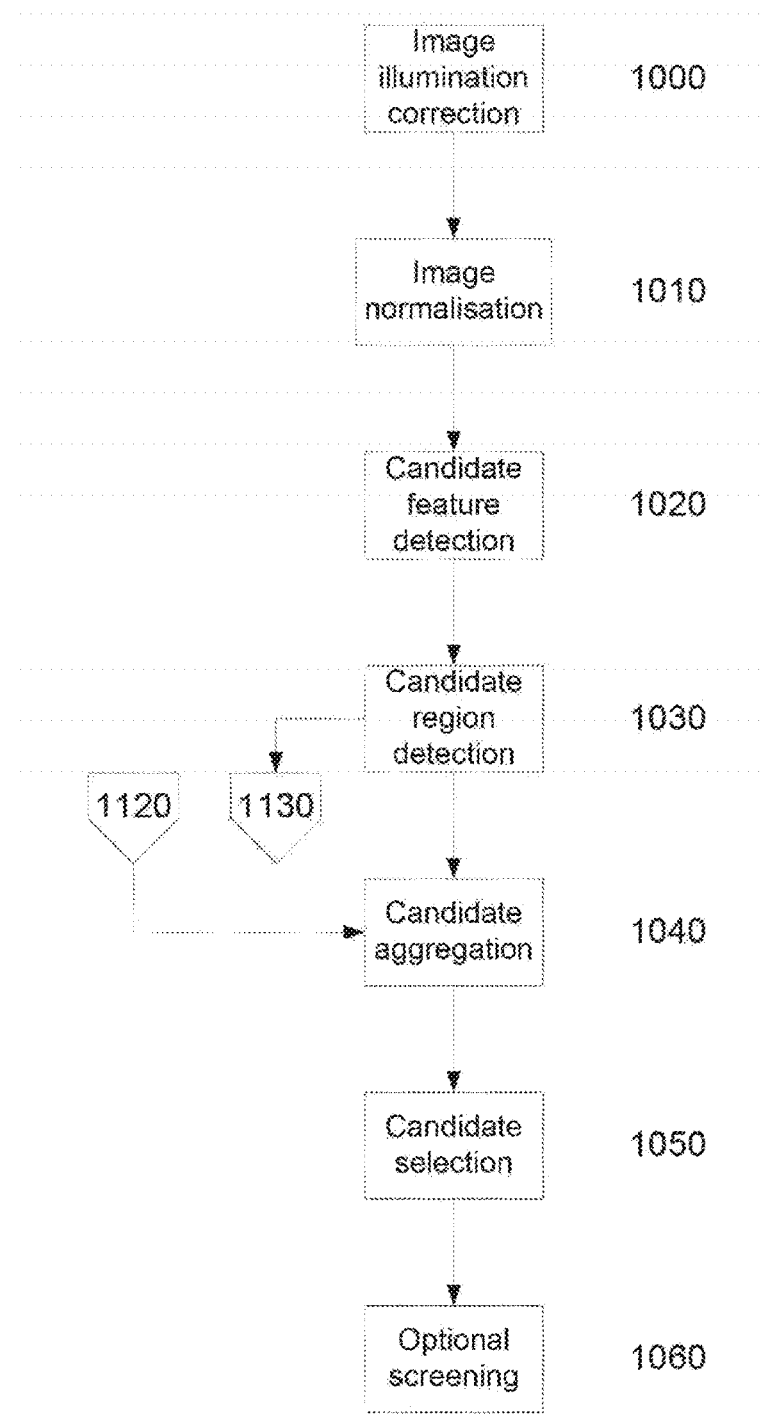
FIG. 10 is a flow chart of an example of a method of microaneurysm (MA) detection.

An example Microaneurysm (MA) detection workflow will now be described with reference to FIG. 10.

In this example, at step 1000 image illumination correction is performed to correct uneven illumination of the image and this can be achieved using standard image processing techniques.

At step 1010 image normalization is performed to remove other imaging artefacts and in particular to ensure images have a standard range of pixel parameters, such as intensities, so that subsequent processing steps can be performed consistently. This can again use standard image processing techniques, and in one example uses a combination of Laplacian of Gaussian filtering and Circular-symmetry filtering.

At step 1020, initial candidate feature detection this is performed to identify candidate features. This in effect performs coarse analysis of the image to identify potential MAs and typically involves examining image pixel parameters, such as the contrast, intensity, hue, saturation, or the like, to identify features within the image that could correspond to MAs.

Initial candidate feature detection typically involves:
 a) Iterative search for an optimal threshold, which involves a comparison of image parameters to threshold values to thereby attempt to identify image features. This can be performed on the basis of multiple different parameters in an iterative fashion, so for example, the process can be performed by examining the intensity of pixels, with thresholds being adjusted in a defined range. It should be noted that this is typically performed on the basis of a green channel image, which best shows features blood vessels.
 b) Rule-based candidate selection which removes features that clearly do not correspond to MAs. A number of different rules can be used and examples of these include:
  i) Removing the candidates with large area that are too large to be MAs. The extent of the large area will vary depending on the implementation and magnification of the image, but is selected to exclude features that are too large to be MAs such as features having an area greater than a threshold. In this regard, MAs typically ranges in size from 25-100 microns, so the threshold will be set slightly above this value; and,
  ii) Removing the candidates close to the image edge to remove candidates that may arise from a larger feature that has been cropped by the edge of the image.

At step 1030, MA region detection is performed using a region-growing method on the initial candidate features to thereby clearly determine the boundary of the candidate features. This is performed by examining neighbouring pixels to pixels in the candidate feature to determine if these are part of the candidate feature. This typically involves comparing the pixel intensity of pixels in the candidate region with neighbouring pixels and excluding neighbouring pixels if the intensity change is more than a certain amount.

Figure 11:
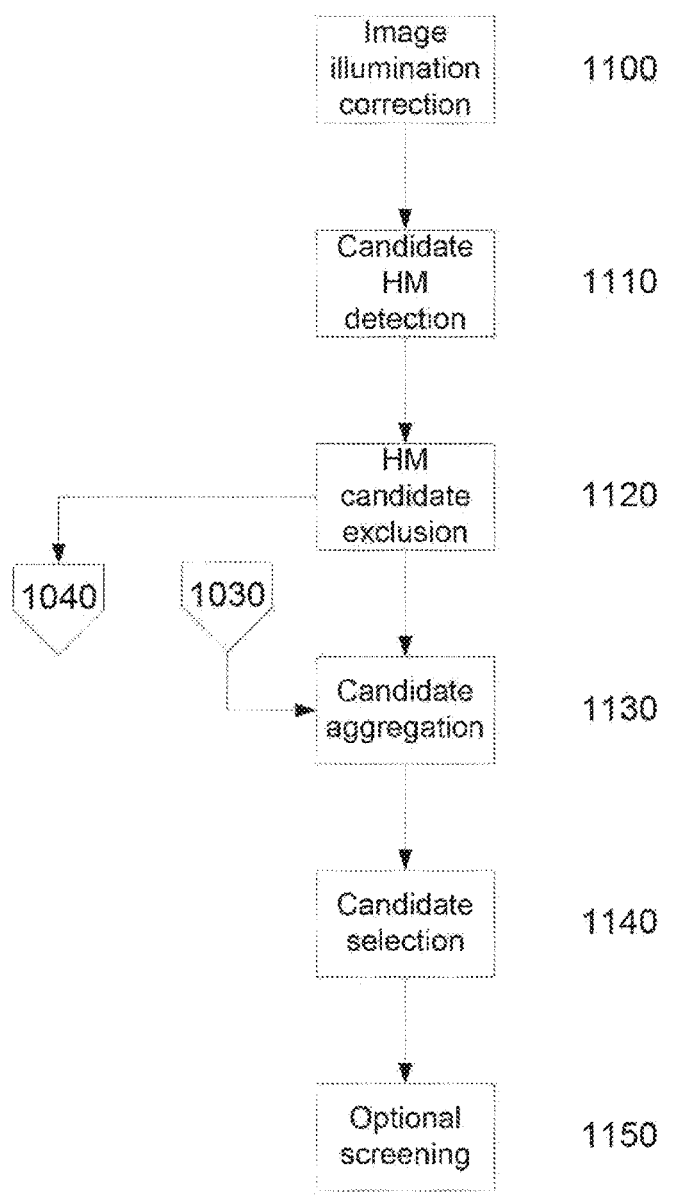
FIG. 11 is a flow chart of an example of a method of Haemorrhage (HM) detection.

At step 1040, candidate features are aggregated with candidate features obtained from the HM detection process, which will be described in more detail below with reference to FIG. 11, to form a final set of MA candidate features. Thus this combines candidate features obtained using two different techniques to ensure any candidate features missed by the above approach, but which are captured by the HM process outlined below, are not excluded from the subsequent stages of analysis (and vice versa). This represents a significant enhancement compared to prior art techniques, in particular by using separate approaches to identify candidate features, this maximises the likelihood that all candidate features and hence all MAs and HMs, will be successfully identified.

At step 1050 candidate features are selected using a rule-based selection criteria. This effectively excludes candidate features that do not meet rule based requirements, thereby limiting the pool of candidate features used for final MA identification. This can be performed on the basis of a range of different attributes of the feature, and in one example involves:

a) Examining the compactness of the candidate to exclude features that are too diffuse to be MAs and would typically involve computing the compactness by the parameters of perimeter and area of the shape to keep the circular-like candidate MA;

b) Examining the contrast of the candidate to determine whether the candidate has an expected contrast compared to the surrounding tissue and hence could be an MA as opposed to another feature. This will typically compare changes in contrast between the candidate and the surrounding tissue and compare this to a predefined threshold range, and, c) Removing the candidates attached with the blood vessels as MAs would not generally be attached to blood vessels that are visible within the image.

Finally, at step 1060 a further optional screening process can be performed by applying a machine learning method to detect true MAs from within the final pool of candidate features. The machine learning method further screens the candidate MAs and examines attributes of these, such as size, shape, pixel intensity, contrast, compactness of shape, principal moment of shape, RGB colour, HSI parameters, or the like, to ascertain whether the candidate features are true MAs.

The machine learning approach can be achieved using any suitable manner as will be appreciated by persons skilled in the art. In one example, this is achieved using a support vector machine (SVM), which can operate, for example, by using a pre-defined training process during which features of MAs confirmed through clinical diagnosis are used to generate an MA training dataset to train the SVM. Then, the trained SVM can be used for true MA identification, as will be appreciated by persons skilled in the art.

Thus, it will be appreciated that the above described process selects a broad range of candidate features and then progressively excludes candidates that do not meet defined requirements, thereby allowing true MAs to be more accurately identified. Once the number and/or location of the MAs have been determined, this information can be used to generate an indicator value, for example indicative of the overall number of MAs, and/or the number of MAs in specific regions or the eye, as shown for example in FIG. 14. This is in turn can be used in the diagnosis of conditions, such as screening for diabetic retinopathy as will be described in more detail below.

An example Haemorrhage (HM) detection workflow will now be described with reference to FIG. 11.

In this example, at step 1100 image illumination correction to correct for uneven illumination. It will be appreciated that this is largely the same as step 1000 described above and that this will not therefore be described in further detail. It will also be appreciated that this step may not need to be performed separately in the event that the MA detection process has already been performed.

At step 1110 initial HM candidate feature detection is performed to act as a coarse analysis of the image to identify potential HMs. This typically is achieved by examining parameters for the image pixels, such as the contrast/intensity/hue/saturation, to identify features within the image that could correspond to HMs. In particular, this process typically includes the following steps:

a) Multi-scale Gaussian enhancement to increase image contrast thereby making candidate features corresponding to HMs easier to identify;

b) Thresholding to compare image parameters to threshold values to thereby attempt to identify image features. This can be performed on the basis of multiple different parameters in an iterative fashion, so for example, the process can be performed by examining the intensity of green channel pixels in turn, in a manner similar to that described above with respect to the MA detection process.

At step 1120, rule-based selection criteria are applied to removes candidate features that clearly do not correspond to HMs. A number of different rules can be used and examples of these include:

a) Examining the area of the candidate exclude candidates having an area that would not correspond to an HM. This will typically exclude features too small or too large to be an HM; and, b) Examining the elongation of the candidate. In particular, as HMs will typically spread out, these generally do not have an elongate shape and hence elongate features are more likely to correspond to blood vessels or the like. Accordingly, this process will typically exclude features whose elongation value is greater than a defined threshold.

Additionally, as part of this process, false HM candidates which correspond to broken segments of blood vessels can be removed. This can be achieved in any suitable manner, such as identifying a central reflex in the feature or comparing with a blood vessel mask, an example of which is shown in FIG. 15B for the image of FIG. 15A and which can be derived using known techniques.

At step 1130, the HM candidate features are aggregated with candidate features derived using the MA detection method described above with respect to FIG. 10. As in the case of the MA detection process, this increases the likelihood that HMs will be detected.

Following this, at step 1140, rule-based selection criteria are applied to select candidate features corresponding to true HMs. This will examine the candidate in different regions using slightly different mechanisms to account for the different optical properties in different areas. Thus for example, pixel parameters can be compared to thresholds, with different thresholds being used in different regions, to thereby improve the correct detection of true HMs identification. Typically this will include separately examining candidates:

a) inside the optic disc region;

b) attached to the blood vessels; and, c) in the fovea region darker than surrounding region.

Finally, at step 1150 an optional machine learning screening process can be used in a manner similar to that described above with respect to FIG. 10, although this is generally not required. Following this, indicator values can be determined, for example on the basis of the total number of HMs, and/or the number of HMs in different regions of the eye.

It will be appreciated from the above that there is typically significant overlap between the MA and HM detection processes, and that these may advantageously therefore be performed in conjunction.

The peripapillary atrophy detection method is used for correct optic disk detection and atrophy detection from colour fundus images. Conventional optic disk detection methods usually include peripapillary atrophy in the optic disk area, thereby reducing the accuracy of optic disk detection. In one example, the peripapillary atrophy detection method uses machine learning methods for pixel and region based classification on the detected optic disk area. The method aims at detecting the correct optic disk boundary while peripapillary atrophy exists, and at the same time, also detecting atrophy information for clinical diagnosis.

Figure 12:
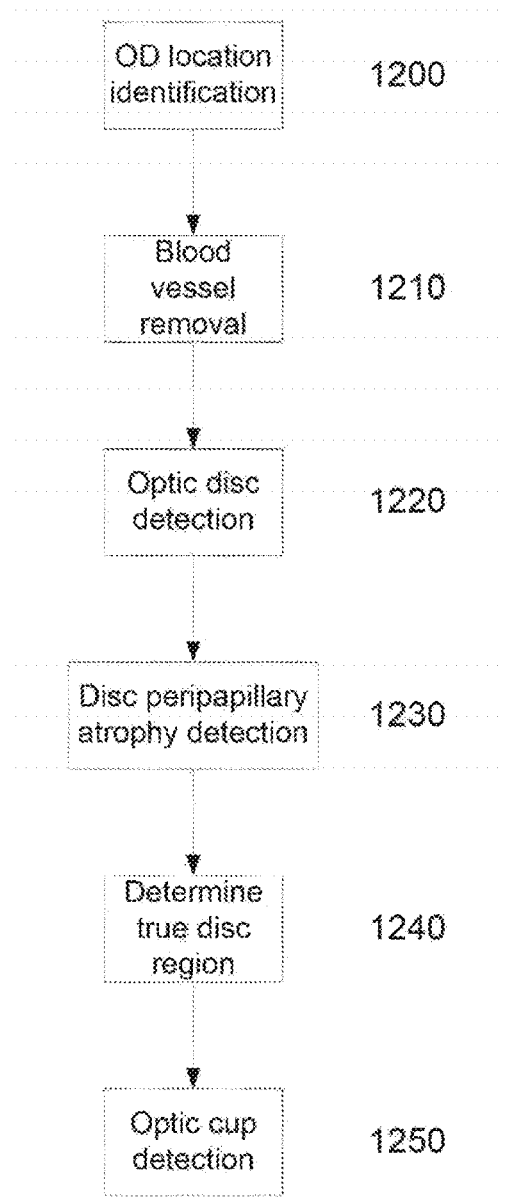
FIG. 12 is a flow chart of an example of a method of retinal optic disc and cup detection.

An example retinal optic disc (OD) and cup detection process will now be described with reference to FIG. 12.

In this example, at step 1200 the location of the OD is determined. This can be achieved using any suitable process such as thresholding the brightness or intensity of pixels and identifying features having a disc shape. At step 1210, blood vessels in the optic disc region are removed from the image using an inpainting algorithm, as known in the art.

At step 1220, the extent of the OD is determined. This can be achieved using any suitable technique, such as region growing or the like. In one example, this is achieved using a 4-quadrant disc detection method which examines quadrants in the vicinity of determined OD.

At step 1230, disc peripapillary atrophy detection is performed. This can be achieved using any suitable technique and in one example uses a combination of approaches to more accurately identify OD atrophy. In particular, the process uses:
  a) Texture feature detection by Gabor filtering;
  b) Image colour information collection; and,
  c) Peripapillary atrophy identification using a machine learning method.

At step 1240 the detected OD region and the detected atrophy region are compared to determine the true OD region. Thus, this will examine the detected OD region and substract from this the atrophy region, allowing the true OD region to be determined.

At step 1250, optic cup detection is performed by examining pixel parameters of pixels within the OD region, allowing the brighter pixels corresponding to the optic cup to be identified. As part of this process, region growing or other similar techniques can be applied to determine the full extent of the optic cup.

Once the optic cup and OD region have been determined, these can be used to establish a numerical value for the cup-to-disc ratio, which can be used as an indicator of the presence of glaucoma. Thus, for example, the ratio can be compared to a predefined threshold, with the result of the comparison being indicative of the presence, absence, degree or extent of glaucoma.

An example bright lesion detection process will now be described with reference to FIG. 13.

In this example, the process involves image illumination correction at step 1300, which is performed in a manner similar to that described above.

At step 1310, initial bright lesion candidate detection is performed, for example using a combination of processes, such as thresholding of pixel image parameters and removal of candidates in the optic disc region to identify candidate features.

Following this at step 1320, rule-based selection criteria are applied to screen the candidate features to determine the true bright lesions. This can be performed using any suitable mechanism, such as a rule based or machine learning method, in a manner similar to that previously described with respect to MA and HM detection, as will be appreciated by persons skilled in the art. This will not therefore be described in further detail.

The blood vessel, optic disk, microaneurysm, haemorrhage and bright lesion detection procedure is used for screening diabetic retinopathy from fundus images. The steps of the procedure are as follows:
  a) An initial retinal blood vessel tree is detected using a blood vessel detecting algorithm 751. The blood vessel area at the optic disk region is refilled by a blood vessel in-painting algorithm in BMEyeLib 743. The optic disk is then detected on a refilled image by the optic disk detecting method adopted by an OpticDiskDetector process 755.
  b) Initial bright areas are detected by a bright area detecting method. The optic disk detected by the OpticDiskDetector process 755 is excluded from the bright areas. The remaining bright areas are then considered to be candidate bright lesions.
  c) The bright lesions are refilled on an original green image by an image in-painting algorithm in BMEyeLib 743. On the refilled image, a more accurate blood vessel tree is detected by a blood vessel detecting method 751.
  d) The microaneurysm and haemorrhage detachment algorithm is then applied on the detected blood vessel tree. Detached microaneurysms and haemorrhages are then detected if they exist, and the final blood vessel tree is obtained excluding these detached "black" lesions.
  e) Initial haemorrhages are detected by a haemorrhage detection algorithm. Detached haemorrhages are included in the initial haemorrhages and form the final haemorrhages.
  f) Initial microaneurysms are detected by a microaneurysm detection method. The detached microaneurysms are then added in with the initial microaneurysms to form the final ones.
  g) The detected candidate bright lesions in step 2) are processed by a machine learning algorithm in BMEyeLib 743. And the true bright lesions are identified.
  h) The detected microaneurysms, haemorrhages and bright lesions are used for early DR grading.

The method for generating DR grading information and formatted dataset includes:
  a) using an automated generated 4-quadrant template and a macular region template to count the distributions of detected microaneurysms, haemorrhages and bright lesions on two visual-field images;
  b) combining the distribution information from two images to generate a formatted dataset (including numbers of lesions in the quadrants and regions and sizes and locations of lesions) for determining the DR severity level and DR oedema severity level grading.

The method for glaucoma scoring includes combining the retinal image processing output (cup-disk ratio and peripapillary atrophy) from the image processing engine 619 and the patient's eye examination results—intra-ocular pressure (e.g. if IOP>15 mmHg), visual field (normal or abnormal), disk asymmetry (e.g. if greater than 0.2), family history, age (over 40), corneal thickness etc.—from the data store engine 623 for glaucoma decision.

It will be appreciated that a wide range of other techniques can also be used for determining an indicator value. For example, this can be achieved by examining blood vessels for abnormalities. This can involve tracking blood vessels based on intensity and/or gradient information, measuring the blood vessel calibre, extracting related features and detecting abnormalities in accordance with at least one of the blood vessel caliber and extracted related features.

The decision support engine 621 uses stored data from the data store engine 623 and the output from the image processing engine 619 to perform decision making on a patient's case. This module consists of the following sub-components to perform the final decision making of a medical case: database analysis, image processing outcome analysis and decision orchestration by rule-based approaches or machine learning mechanism The database analysis uses the stored data to analyse the patient's existing records and previous diagnosis information and produce disease specific parameters for analysis. Data analysis includes:

a) Change of blood glucose levels
b) Vital signs
c) Weight levels
d) Nutrition intake levels
e) ECG signals
f) Genetic information The image processing outcome analysis is based on the output of the image processing engine 619. This component produces a quantitative outcome for a particular case.

The decision orchestrator component combines the database analysis and image processing analysis and produces a human readable decision for the particular patient's case. The analysis mechanism combines the rule-based decision and machine learning based decision.

The basic workflow related to the decision support engine 621, is shown in FIG. 16, and essentially entails receiving the image processing engine output for a particular patient at step 1671, and the data store engine output for the same patient at step 1673, performing a data analysis on the combined data at step 1675 and undertaking disease grading at step 1677.

In this regard, the output from the image processing engine and the data store engine are analysed using a decision support engine that implements a rule based approach, allowing a disease grading to be determined. This typically involves comparing the indicator value determined from the workflows outlined above, such as a number of MAs, HMs or bright lesions, or an optic disc-to-cup ratio, to one or more defined thresholds, which are indicative of a particular disease state. The thresholds can be patient specific, for example based on previous measurements for a subject, to thereby provide a longitudinal outcome, or can be based on value established from a reference population having a range of different stages of conditions of interest.

The output from the image processing engine can be either file based or memory based, with the decision support engine reading information from the data store and the image processing engine and store the results back in the datastore as required. This information can be accessed by client applications on the client devices, with image processing output and/or disease grading being shown besides the image. This allows operators of the client device to view the original image, derived indicator values and the result of the disease grading, allowing them to understand the assessment outcome and optionally explain this to the subject. These interfaces are implemented through standard web service (SOAP/XML/JSON) allowing them to be accessed across various devices and client applications. User access permissions can then be handled within the web services.

The data store engine 623 includes a database management system for accessing and managing a distributed data store for storing data selectively in multiple locations and caching same for rapid retrieval.

Data storage will grow exponentially when new services are provided and so the data store engine is designed to manage the data in a way such that the data is stored in multiple locations and is cached for performance improvements. Such implementations are commercially available from MSSQL Database replication.

Figure 17:
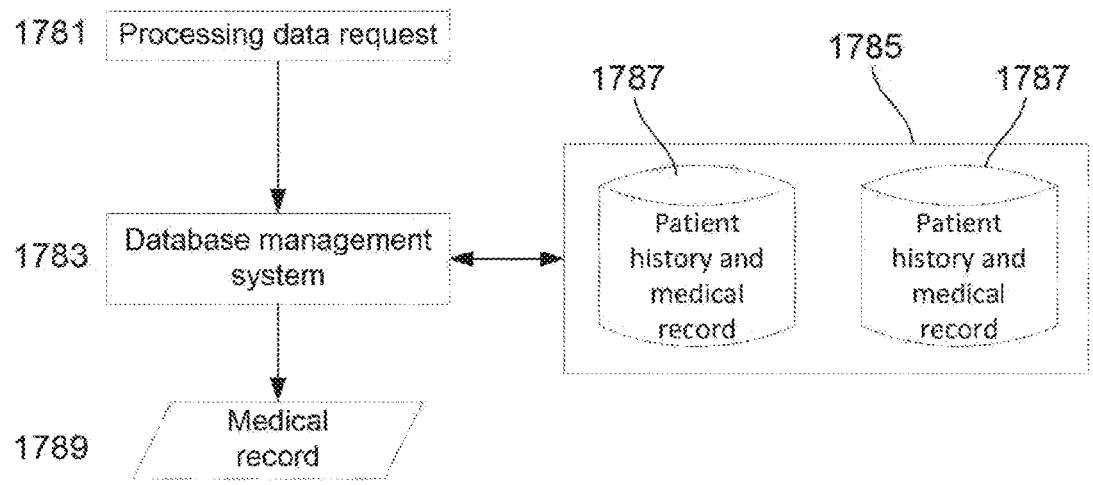
FIG. 17 is a high level flow chart showing the operation of the data store engine; and, FIG. 18 is a high level flow chart showing the operation of the billing engine.

The general process flow adopted by the data store engine 623, as shown in FIG. 17, entails receiving a process data request at step 1781, invoking the database management system at step 1783 to access the distributed data store 1785 that contains patient history and medical records 1787 at multiple locations to retrieve the applicable patient history and medical records of a particular patient being diagnosed, and output same as a medical record file at step 1789 for use by the decision support engine 621.

To avoid issues with merging of records from multiple remote databases, system can implement unique identifiers in all tables to thereby assist in merging records. In this regard, records relating to a common subject will typically be identified using the subject identifier. Thus, when records from different sources are merged, these can be aligned based on the subject identifier, whilst allowing merging to be performed using the unique database identifiers.

The billing engine 625 is implemented within the host server in a manner so that it handles all the billing services for the consumers of the system. This service module will include various service providers and consumers.

Figure 18:
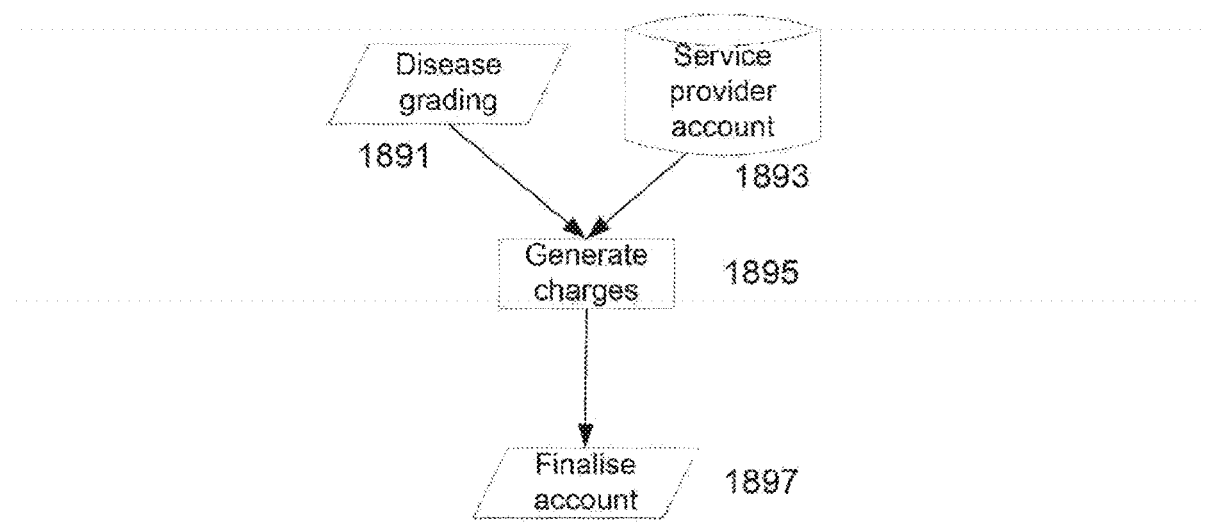

The overall flowchart of the billing engine 625, is shown in FIG. 18, and involves receiving the particular disease grading from the decision support engine 621 at step 1891, generating charges for the patient using a designated service provider account 1893 at step 1195, and finalising the account at step 1897. Billing agreements can be purchased in advance or as per request on the fly. Different billing models can be applied (eg: Per patient, Monthly, per site), depending upon the service provider requirements.

The specialists group component 617 involves incorporating a group of specialists to provide support services on diagnosis for various disease conditions. When the advice of a specialist is requested by the client site 615 or through a discrepancy on the host server side of the system, the server is designed to redirect the specific patient case and related medical records to a dedicated specialist who will be a part of the specialist group. These specialist group members will be on call and will get notified on any new episode by the host server. On receiving notification at step 641, the notified specialist uses their web browser or mobile devices to invoke their specialist client application to log in to the cloud based services component 613 review and complete their assessment of the patient from the information generated by the decision support engine 621 at steps 643 and 645, and send their expert opinion on the case back to the host server.

With respect to the administrative client site component 615, each administrator client connects to the server via industry standard secured web connections through various devices. The client site technologies include industry standard technologies such as:

a) Medical imaging devices and measurement devices
b) Mobile applications for data collection using mobile/cell phones and mobile devices which transmit data
c) Tablet devices.
d) Laptops.

The administrative client site also has video conferencing facilities built into the system which allows the patient/clinicians to connect to the specialist or the care giver for advice.

The client site also is designed to support offline storage of medical information for rural screening requirements, which allows the consumers and providers to connect to the cloud and synchronise the data when the network connectivity is restored using known store and forward telemedicine techniques. This allows for smooth operations on rural screening environments.

As shown in FIG. 6, the general workflow of the administrator client site component 615 involves a patient visiting at step 651, performing an initial clinical data gathering at step 653, generating and eRecord in relation to such at step 655, and sending same to the host server for the diagnosis to be performed by the cloud based services component 613. Once the diagnosis is completed, it is sent by the host server to the be received by the administrative client site 615 at step 657 and then actioned appropriately at step 659.

It should be appreciated that the present invention has several advantages over previous telemedicine based systems. In particular, the cloud based server structure allows a well-defined screening technique for various disease conditions to be introduced in a seamless manner and allows for any person or organisation to consume the service using a standardised medical approach. This is performed having access to powerful image processing and machine learning algorithms and additional specialist group support to provide expert assessment using the cloud.

Several specialist locations may be disconnected away from the cloud based system due to network outage or network unavailability. The system is designed in such a way that the specialist locations can operate independently despite of the outage and continue on providing services to the client without any disruptions (offline system).

In this regard, offline operation typically relies on remote storage of data, such as subject or image data, in a local datastore at the client side until the data can be transferred to the server side for analysis. In this regard, the client side datastore can connect to the server datastore and synchronize the medical records. When the network between the client and the server gets interrupted the datastore is designed to continue to work and will hold the data. When the network is restored the datastores will automatically synchronize and keep the patient record consistent.

Furthermore, when offline, the client applications operate without a network connection to continue the screening procedure without interruption. To achieve this, the client application users can connect to an imaging device and add subject data and the relevant images to a record. This record is then encrypted and saved on to the local computer. These encrypted files can only be read from the cloud based system and synchronised with the server side using the unique identifiers without breaking the consistency of the existing datastore.

Whilst the above described systems have been described with respect to network based systems, it will be appreciated that similar processes can be performed in a stand-alone device.

In one example, a system can be provided for use in medical diagnosis of a biological subject, the system including one or more electronic processing devices that determines image data indicative of at least one image of part of the subject's eye, uses at least one analysis process to quantify at least one feature in the image data and generates an indicator value indicative of the quantified at least one feature, the indicator value being used in the assessment of a condition status of at least one condition. This can be integrated into a hand-held imaging device, thereby allowing an immediate diagnosis indication to be provided to the subject.

The term subject includes any living system, and in particular can include human, or non-human subjects. Thus, whilst the above examples have focussed on a subject such as a human, it will be appreciated that the apparatus and techniques described above can be used with any animal, including but not limited to, primates, livestock, performance animals, such as race horses, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A system for use in remote medical diagnosis of a biological subject, the system including one or more electronic processing devices that:
    a) receive image data indicative of at least one image of part of the subject's eye from a client device via a communications network;
    b) review subject data indicative of at least one subject attribute;
    c) select at least one analysis process using results of the review of the subject data;
    d) uses the analysis process to quantify at least one feature in the image data; and,
    e) generate an indicator value indicative of the quantified at least one feature, the indicator value being used in the assessment of a condition status of at least one condition;
    wherein, as part of the analysis, the one or more processing devices perform retinal optic disc and cup detection by:
        i. determining an optic disc location in the image;
        ii. removing blood vessels from the optic disc region by in-painting;
        iii. detecting an optic disc region;
        iv. detecting an optic disc atrophy region;
        v. comparing the optic disc region and optic disc atrophy region to determine a true optic disc region; and
        vi. performing optic cup detection.

2. The system according to claim 1, wherein the one or more electronic processing devices:
    a) analyse the image data to identify at least one type of feature; and,
    b) quantify a number of incidences of the at least one type of feature.

3. The system according to claim 2, wherein the one or more electronic processing devices:
    a) segment the image of at least part of the eye; and,
    b) quantify a number of incidences of the at least one type of feature in each segment of the image.

4. The system according to claim 1, wherein the one or more electronic processing devices:
    a) compare the indicator value to at least one threshold, wherein the threshold is at least partially based on at least one of:
        i) at least one previous indicator value for the subject; and,
        ii) indicator values measured for a reference population; and, b) generate a notification in accordance with the results of the comparison, wherein the notification is at least one of:
  i) indicative of a condition status;
  ii) a referral requirement; and,
  iii) used at least in part to initiate a video conference between the client device and a specialist device.

5. The system according to claim 1, wherein the one or more processing devices transfer an indication of at least one of the indicator value and a notification to the client device for display.

6. The system according to claim 1, wherein the client device includes:
  a) an imaging device that captures an image of at least part of the eye of the subject, wherein the image data is indicative of at least one of:
    i) at least one color fundus image; and,
    ii) an image sequence showing pupil response; and,
  b) at least one computing system in communication with the imaging device that transfers image data to the one or more electronic processing devices, wherein the one or more processing devices:
    i) perform image quality assessment; and,
    ii) selectively analyze the image in accordance with the results of the quality assessment.

7. The system according to claim 1, wherein the condition status is at least one of a presence, absence, degree or prognosis of a condition.

8. The system according to claim 1, wherein the system includes at least one store that stores a number of stored analysis processes for different screening conditions and wherein the one or more electronic processing devices:
  a) review the subject data to determine at least one screening condition; and,
  b) select at least one analysis process from the number of stored analysis processes in accordance with the at least one screening condition.

9. The system according to claim 1, wherein at least one of:
  a) the subject data includes an indication of at least one of:
    i) at least one behavioral attribute;
    ii) at least one phenotypic attribute;
    iii) at least one genetic attribute;
    iv) at least one medical intervention;
    v) at least one previous condition;
    vi) at least one previous indicator value; and,
    vii) part of a medical record;
  b) the features include at least one of:
    i) microaneurysms;
    ii) haemorrhages;
    iii) lesions; and,
    iv) retinal vessel features; and,
  c) the indicator value is indicative of at least one of:
    i) optic disc atrophy;
    ii) a number of lesions;
    iii) a number of detached microaneurysms;
    iv) a number of detached haemorrhages; and,
    v) vessel abnormalities; and,
  d) the indicator value is used in the diagnosis of at least one of:
    i) Glaucoma;
    ii) Age Related Macular degeneration;
    iii) diabetic retinopathy;
    iv) Alzheimer's disease;
    v) stroke;
    vi) hypertension; and,
    vii) cardio vascular disease.

10. The system according to claim 1, wherein the one or more processing devices perform image quality assessment by:
  a) determining a retinal region mask from the image data;
  b) performing image illumination correction to correct for uneven image illumination;
  c) detecting bright reflection regions;
  d) determining blood vessel distribution;
  e) detecting image histogram of the whole retinal region and sub-regions using the region mask; and,
  f) performing image quality assessment by evaluating at least one of:
    i) the retinal region mask;
    ii) bright reflection regions;
    iii) whole retinal region histogram;
    iv) sub-region histograms; and,
    v) blood vessel distribution.

11. The system according to claim 10, wherein the one or more processing devices identify blood vessels by:
  a) enhancing the image using linear structuring element processing;
  b) detecting blood vessel masks based on associated blood vessel detecting thresholds; and,
  c) calculating blood vessel distribution in sub-regions of the image.

12. The system according to claim 1, wherein the one or more processing devices perform microaneurysm detection by:
  a) detecting candidate features in the image; and,
  b) selectively excluding candidate features in accordance with at least one of:
    i) candidate feature size; and,
    ii) candidate feature location; and,
  c) identifying microaneurysms at least partially in accordance with remaining candidate features.

13. The system according to claim 12, wherein the one or more processing devices perform at least one of:
  a) detect candidate features in accordance with pixel parameters of image pixels;
  b) determine candidate feature boundaries using region growing;
  c) aggregate candidate features with candidate features from a haemorrhage detection process;
  d) identify microaneurysms using at least one of:
    i) a rule based selection of candidate features; and,
    ii) a machine learning algorithm;
    iii) candidate feature attributes including at least one of:
      (1) compactness;
      (2) contrast;
      (3) pixel hue, saturation or intensity;
      (4) shape;
      (5) size; and,
      (6) connection to blood vessels.

14. The system according to claim 1, wherein the one or more processing devices perform at least one of:
  a) image normalization; and,
  b) image illumination correction.

15. The system according to claim 1, wherein the one or more processing devices perform at least one of:
  a) haemorrhage detection by:
    i) detecting candidate features in the image; and,
    ii) selectively excluding candidate features in accordance with at least one of:
      (1) candidate feature size; and,
      (2) candidate feature shape; and,
    iii) identifying haemorrhages at least partially in accordance with remaining candidate features;

b) detect candidate features by:
   i) increasing image contrast; and,
   ii) comparing image pixel parameters to threshold values;
   iii) aggregate candidate features with candidate features from a microaneurysm detection process; and,
c) identify haemorrhages using at least one of:
   i) a rule based selection of candidate features; and,
   ii) a machine learning algorithm.

16. The system according to claim 1, wherein the one or more processing devices perform at least one of:
    a) detect the optic disc atrophy region using at least one of:
       i) texture feature detection;
       ii) image colour information; and,
       iii) machine learning using one or more optic disc attributes; and,
    b) use the true optic disc region and optic cup to determine at least one of:
       i) a cup-disk ratio; and,
       ii) peripapillary atrophy.

17. The system according to claim 1, wherein the one or more processing devices perform at least one of:
    a) bright lesion detection by:
       i) detecting candidate features in the image; and,
       ii) selectively excluding candidate features in an optic disc region; and,
    b) blood vessel abnormality analysis by:
       i) tracking blood vessels according to at least one of intensity and gradient information;
       ii) measuring the blood vessel caliber;
       iii) extracting related features; and,
       iv) detecting abnormalities in accordance with at least one of the blood vessel caliber and extracted related features.

18. The system according to claim 1, wherein the client device includes a datastore and wherein the client device:
    a) generates a record including at least one of:
       i) the image data;
       ii) a subject identifier; and,
       iii) subject data;
    b) encrypts the record;
    c) stores the encrypted record in the datastore; and,
    d) transfers the encrypted record to the one or more processing devices.

19. A method for use in remote medical diagnosis of a biological subject, the method including, in one or more electronic processing devices:
    a) receiving image data indicative of at least one image of part of the subject's eye from a client device via a communications network;
    b) reviewing subject data indicative of at least one subject attribute;
    c) performing at least one analysis process comprising retinal optic disc and cup detection by:
       i. determining an optic disc location in the image;
       ii. removing blood vessels from the optic disc region by in-painting;
       iii. detecting an optic disc region;
       iv. detecting an optic disc atrophy region;
       v. comparing the optic disc region and optic disc atrophy region to determine a true optic disc region; and
       vi. performing optic cup detection;
    d) using the analysis process to quantify at least one feature in the image data; and,
    e) generating an indicator value indicative of the quantified at least one feature, the indicator value being used in the assessment of a condition status of at least one condition.

* * * * *